US005497763A

United States Patent [19]

Lloyd et al.

[11] Patent Number: 5,497,763

[45] Date of Patent: Mar. 12, 1996

[54] DISPOSABLE PACKAGE FOR INTRAPULMONARY DELIVERY OF AEROSOLIZED FORMULATIONS

[75] Inventors: Lester J. Lloyd, Orinda; Peter M. Lloyd, Oakland; Reid M. Rubsamen, Berkeley, all of Calif.

[73] Assignee: Aradigm Corporation, Hayward, Calif.

[21] Appl. No.: 166,972

[22] Filed: Dec. 14, 1993

Related U.S. Application Data

[63] Continuation-in-part of Ser. No. 65,660, May 21, 1993.

[51] Int. Cl.$^6$ .................................................. A61M 11/00

[52] U.S. Cl. ................................ 128/200.14; 128/200.16

[58] Field of Search ......................... 128/200.14, 203.21, 128/200.16; 206/363

[56] References Cited

U.S. PATENT DOCUMENTS

| | | | |
|---|---|---|---|
| 3,187,748 | 6/1965 | Mitchell et al. | 128/200.23 |
| 3,565,070 | 2/1971 | Hanson et al. | 128/200.23 |
| 3,658,059 | 4/1972 | Steil | 128/200.21 |
| 3,812,854 | 5/1974 | Michaels et al. | 128/200.16 |

(List continued on next page.)

FOREIGN PATENT DOCUMENTS

| | | |
|---|---|---|
| 0186280 | 10/1985 | European Pat. Off. . |
| 0530625 | 3/1993 | European Pat. Off. . |
| 0541127 | 5/1993 | European Pat. Off. . |
| 0546607 | 6/1993 | European Pat. Off. . |
| 8121383 | 5/1983 | France . |
| 2837040 | 2/1980 | Germany . |

(List continued on next page.)

OTHER PUBLICATIONS

Baum, E. A. et al., "A novel breath actuated piezo electronic inhaler" 3M Healthcare Product Bulletin, 3M House, Morley Street Loughborough. Leic S LE11 1EP, England (1 page total).

Byron, P. R., ed., *Respiratory Drug Delivery* CRC Press, Inc., Boca Raton, FL, (1990).

Costar™ Life Science Filtration Catalog, "Nucleopore™ Polycarbonate Membranes" (1992) p. 7.

Newman et al., "Deposition of pressurised aerosols in the human respiratory tract" *Thorax* (1981) 36:52–55.

Newman et al., "Deposition of pressurised aerosols in the lung using radio–labelled particles" *Thorax* (1980) 35:234.

Newman et al., "How should a pressurized β–adrenergic bronchodilator be inhaled?" *Eur. J. Respir. Dis.* (1981) 62:3–21.

Newman et al., "Deposition of pressurized suspension aerosols inhaled through extension devices[1–3] " *Am. Rev. Respir. Dis.* (1981) 124:317–320.

*Primary Examiner*—Aaron J. Lewis

*Attorney, Agent, or Firm*—Karl Bozicevic; Fish & Richardson

[57] ABSTRACT

A disposable package is provided which makes it possible to hold and disperse therefrom liquid, flowable formulations including aqueous formulations (solutions or dispersions with particles less than 0.25 microns in diameter) of a pharmaceutically active drug. The formulation is packaged in individual dosage unit containers which containers are preferably interconnected. The package is designed to be integrated into a cassette which can be loaded into a dispersing device capable of individually opening dosage unit containers and aerosolizing the contents through a porous membrane, into a mouth piece on the cassette, for delivery to a patient. In addition to and alongside of each porous membrane, the package preferably includes one or more openings through which air is forced in order to aid in avoiding the accumulation of aerosolized particles. The package is configured so that the formulation is held in a container not positioned directly vertical to and below the porous membrane, thus making it necessary to channel formulation horizontally to the porous membrane and making it possible to include a vibrating mechanism directly below a chamber covered by the porous membrane. Release of aerosolized drug is breath actuated in a manner so as to provide for repeatable dosing of drug to the patient.

21 Claims, 11 Drawing Sheets

U.S. PATENT DOCUMENTS

| | | | |
|---|---|---|---|
| 3,814,297 | 6/1974 | Warren | 222/402.13 |
| 3,826,413 | 7/1974 | Warren | 222/402.13 |
| 3,991,304 | 11/1976 | Hillsman | 364/413.04 |
| 4,361,401 | 11/1982 | Smith, Jr. et al. | 356/36 |
| 4,465,234 | 8/1984 | Maehara et al. | 239/102.2 |
| 4,484,577 | 11/1984 | Sackner et al. | 128/203.28 |
| 4,533,082 | 8/1985 | Maehara et al. | 239/102.2 |
| 4,592,348 | 6/1986 | Waters, IV et al. | 128/200.23 |
| 4,604,847 | 8/1986 | Moulding, Jr. et al. | 53/75 |
| 4,627,432 | 12/1986 | Newell et al. | 128/203.15 |
| 4,648,393 | 3/1987 | Landis et al. | 128/200.23 |
| 4,677,975 | 7/1987 | Edgar et al. | 128/200.14 |
| 4,790,305 | 12/1988 | Zoltan et al. | 128/200.23 |
| 4,790,479 | 12/1988 | Matsumoto et al. | 239/102.2 |
| 4,803,978 | 2/1989 | Johnson, IV et al. | 128/200.23 |
| 4,852,582 | 8/1989 | Pell | 128/716 |
| 4,877,989 | 10/1989 | Drews et al. | 128/200.16 |
| 4,896,832 | 1/1990 | Howlett | 239/322 |
| 4,926,852 | 5/1990 | Zoltan et al. | 128/200.23 |
| 5,152,456 | 10/1992 | Ross et al. | 239/102.2 |

FOREIGN PATENT DOCUMENTS

| | | |
|---|---|---|
| 4133274 | 2/1993 | Germany . |
| 1518998 | 7/1978 | United Kingdom . |
| 2104393 | 3/1983 | United Kingdom . |
| 2255918 | 11/1992 | United Kingdom . |
| WO90/13327 | 11/1990 | WIPO . |
| WO91/14468 | 10/1991 | WIPO . |
| WO92/11050 | 4/1992 | WIPO . |
| WO92/07599 | 5/1992 | WIPO . |
| WO92/09322 | 6/1992 | WIPO . |
| WO93/03785 | 3/1993 | WIPO . |
| WO93/09832 | 5/1993 | WIPO . |
| WO93/17728 | 9/1993 | WIPO . |

DISPOSABLE PACKAGE FOR INTRAPULMONARY DELIVERY OF AEROSOLIZED FORMULATIONS

CROSS-REFERENCES

This application is a continuation-in-part of our earlier filed U.S. application Ser. No. 08/065,660 filed May 21, 1993, pending, which application is incorporated herein by reference and to which application we claim priority under 35 U.S.C. § 120.

FIELD OF THE INVENTION

This invention relates generally to methods of drug delivery, containers and systems used in the intrapulmonary delivery of drugs. More specifically, the invention relates to a disposable package in the form of two or more containers which containers are loaded into a cassette for use in the controlled delivery of flowable, liquid formulations and to devices used to carry out the methods.

Background of the Invention

The intrapulmonary delivery of pharmaceutically active drugs is accomplished by two distinct methodologies. In accordance with one method, a pharmaceutically active drug is dispersed in a low boiling point propellant (a CFC or HFC) and loaded in a pressurized canister from which the drug/propellant formulation may be released by the use of a device generally known as a metered dose inhaler (MDI). Once released, the propellant evaporates and particles of the drug are inhaled by the patient. The other method involves the use of a nebulizer which creates a mist of fine particles from a solution or suspension of a drug which mist is inhaled by the patient. Both methods are hindered by significant problems relating to patient compliance and dosing as described further below.

Metered dose inhalers that are generally manually operated and some breath actuated devices have been proposed and produced. Breath actuated inhalers typically contain a pressurized propellant and provide a metered dose automatically when the patient's inspiratory effort either moves a mechanical lever or the detected flow rises above a preset threshold, as detected by a hot wire anemometer. See, for example, U.S. Pat. Nos. 3,187,748; 3,565,070; 3,814,297; 3,826,413; 4,592,348; 4,648,393; 4,803,978; 4,896,832; and a product available from 3M Healthcare known as Aerosol Sheathed Actuator and Cap.

A major problem with manual metered dose inhalers is that the patient frequently actuates the device at the incorrect point during the breathing cycle to obtain the benefits of the intended drug therapy or breathes at the wrong flow rate. Thus, patients may inspire too little medication, or take a second dose and receive too much medication. The problem is, therefore, the inability to administer precise dosages.

Another problem with metered dose inhalers is that the devices include low boiling point propellants such as halohydrocarbons and halocarbons which have adverse environmental effects. Further, other low boiling point propellants are not desirable in that they may have adverse medical effects on patients.

A problem with breath activated drug delivery is that the dose is triggered on crossing a fixed threshold inspiratory effort. Thus, an inspiration effort may be sufficient to release a metered dose, but the inspiratory flow following the release may not be sufficient to cause the aerosol medication to pass into the desired portion of the patient's airways. Another problem exists with patients whose inspiratory effort is not sufficient to rise above the threshold to trigger the release valve at all. Yet another problem is that the particle size can vary greatly and larger particles cannot enter the smaller lung passages and therefore are not delivered to the same degree and/or rate as are smaller particles. Any of these problems can make it difficult or impossible to monitor the delivery of a precise dosage of medication to a patient.

Attempts have been made to solve the patient inspiration synchronization problem. U.S. Pat. No. 4,484,577 refers to using a bidirectional reed whistle to indicate to the patient the maximum rate of inhalation for desired delivery of the drug and flow restrictor to prevent the patient from inhaling too rapidly. U.S. Pat. No. 3,991,304 refers to using biofeedback techniques to train the patient to adopt a desired breathing pattern. U.S. Pat. No. 4,677,975 refers to using audible signals and preselected time delays gated on the detection of inspiratory flow to indicate to the patient when to inspire and expire, and delivering inhalable material a selected time after the detected onset of flow. However, these devices also suffer from improper operation by patients who are not properly trained or do not conform their breathing to the instructed breathing pattern and whose inspiratory flow does not provide adequate delivery of the medication. Such problems make reproducible delivery of predetermined dosages virtually impossible.

Studies in Byron (ed.), *Respiratory Drug Delivery,* CRC Press, Inc. (1990); Newman et al., *Thorax,* 1981, 36:52–55; Newman et al., *Thorax,* 1980, 35:234; Newman et al., *Eur. J. Respir. Dis.,* 1981, 62:3–21; and Newman et al., *Am. Rev. Respir. Dis.,* 1981, 124:317–320 indicate that during a single breath of an aerosol compound, only about ten percent of the total aerosol material presented is deposited into the lungs and that the location of deposition in the lung depends upon (1) breath parameters such as volume of inspiration, inspiratory flow rate, inspiratory pause prior to expiration, the lung volume at the time the bolus of medication is administered, and expiratory flow rate, (2) the size, shape and density of the aerosol particles (i.e., the medicinal compound, any carrier, and propellant), and (3) the physiological characteristics of the patient. Present devices and methods cannot eliminate these variables and as such cannot control dosage administration.

A problem with existing metered dose inhalers, whether or not breath actuated, is that they are factory preset to deliver a fixed dose at a given particle size distribution. Such devices are not capable of reducing the dose to reflect improvement in the patient's condition, or selecting a maximum desired respirable fraction of the aerosol mist that is suitable for a desired location of delivery of the medication in the particular patient.

Devices for controlling particle size of an aerosol are known. U.S. Pat. No. 4,790,305 refers to controlling the particle size of a metered dose of aerosol for delivery to the walls of small bronchi and bronchioles by filling a first chamber with medication and a second chamber with air such that all of the air is inhaled prior to the inhaling medication, and using flow control orifices to control the flow rate. U.S. Pat. No. 4,926,852 refers to metering a dose of medication into a flow-through chamber that has orifices to limit the flow rate to control particle size. U.S. Pat. No. 4,677,975 refers to a nebulizer device that uses baffles to remove from any aerosol particles above a selected size. U.S. Pat. No. 3,658,059 refers to a baffle that changes the size of an aperture in the passage of the suspension being inhaled to select the quantity and size of suspended particles delivered. A problem with these devices is that they process the aerosol after it is generated and thus are inefficient and wasteful.

It is well known that pulmonary functions, such as forced expiratory volume in one second, forced vital capacity, and peak expiratory flow rate, can be measured based on measured flow rates and used to (1) diagnose the existence of medical conditions, (2) prescribe medication, and (3) ascertain the efficiency of a drug therapy program. See, for example, U.S. Pat. Nos. 3,991,304 and 4,852,582 and the publications of Newman et al. discussed above. Heretofore, these tests have been performed using available spirometers. U.S. Pat. No. 4,852,582 also refers to using a peak flow rate meter to measure changes in peak flow rate before and after administration of a bronchodilator. The results of such tests before and after administration of several different medications are used to evaluate the efficiency of the medications.

A problem with the foregoing pulmonary function test devices is that they are too complicated for most patients to use effectively and obtain repeated delivery of a given amount of drug i.e. user error in administration causes significant variability in the amount of drug the patient receives. Another problem is that the data obtained does not directly effect the operation of the device, i.e. it must be examined and interpreted by a trained medical practitioner to be meaningful. Another problem is that they do not provide adequately for altering the dosage of the medication administered in a single patient during the course of therapy, or from patient to patient, using the same delivery device for generating an aerosol of the same or different medications.

Attempts have been made to solve many of the above-referred-to problems. However, inconsistent user compliance combined with undesirably large particle size continues to cause problems with obtaining precise dosing.

Nebulizers utilize various means in order to create a fog or mist from an aqueous solution or suspension containing a pharmaceutically active drug. The mist created by the nebulizer device is directed towards the face of the patient and inhaled through the mouth and nose. Nebulizer devices and methodology can be quite useful when the precise dosing of the drug being delivered to the patient is not of particular importance. For example, in some situations the nebulizer creates a mist from an aqueous solution containing a bronchodilator which can be inhaled by the patient until the patient feels some improvement in lung function. When precise dosing is more important the nebulizer device and delivery methodology suffers from many of the disadvantages of metered dose inhaler devices and methodology as described above. In addition, nebulizers are large in size and not hand-held, easily transportable devices like MDIs. Accordingly, a nebulizer can only be used within a fixed location such as the patient's home, the doctor's office and/or hospital. However, a portable nebulizer is taught in published PCT application WO92/11050 incorporated herein by reference. Another nebulizer which uses a high frequency generator to create an aerosol is described in U.S. Pat. No. 3,812,854 issued May 28, 1974. Drug formulations placed in nebulizers are generally diluted prior to delivery. The entire diluted formulation must generally be administered at a single dosing event in order to maintain the desired level of sterility and the nebulizer cleaned after use. Yet another disadvantage of nebulizers is that they produce an aerosol which has a distribution of particle sizes not all of which are of appropriate size to reach the targeted areas of the lung. The present invention endeavors to address and solve these and other problems.

Summary of the Invention

A disposable package is provided which makes it possible to hold and disperse therefrom liquid, flowable formulations, e.g. aqueous and alcohol based formulations of a pharmaceutically active drug. The formulation is placed in individual dosage unit containers which containers are preferably interconnected to form a cellular array of interconnected packages which can be loaded into a cassette which cassette preferably includes a channel which forms a mouth piece integral therewith. The cassette is designed to be integrated into a dispersing device capable of individually opening dosage unit containers and aerosolizing the contents through a porous membrane, into the mouth piece, for delivery to a patient. In addition to and alongside of each porous membrane, the package (or cassette or device) preferably includes one or more openings through which air is forced in order to aid in avoiding the aggregation or accumulation of aerosolized particles. The package is configured so that the formulation is held in a container not positioned directly vertical to and below the porous membrane, thus making it necessary to channel formulation horizontally to the porous membrane and making it possible to include a vibrating mechanism with variable vibration frequency (in the cassette or dispersing device) directly below a resonance chamber covered by the porous membrane. In this way, the resonance cavity in contact with the vibrating mechanism will be in a fixed position or has a fixed resonant characteristic during the dispersion of formulation, e.g. while the dosage unit container is collapsed. The pores of the membrane are preferably cone shaped to reduce the force needed to move formulation therethrough, and the membrane is preferably comprised of a hydrophobic material. The cone shaped pores of the membrane, at the narrowest point, have a diameter of about 0.25 micron to 6 microns and the dispensing device includes a piezoelectric crystal for vibrating which creates a vibration frequency directly below a chamber positioned below the porous membrane such that formulation forced through the porous membrane is aerosolized to particles having a diameter of about 0.5 micron to 12 microns. The vibrating devices include not only piezoelectric crystals but materials such as a piezoelectric polymer such as Kynar®, which is a thin film material with piezoelectric properties sold commercially by Pennwalt Corporation. The holes in any given membrane may all be the same size or may be different in size within a fixed range.

The packages are preferably interconnected on a tape-like connecting means and folded or wound in the cassette in a manner which allows the dispensing device to successively move from a first package to a second (after dispersing formulation from the first container) and successively move to other packages as needed until the desired amount of drug has been dispersed, aerosolized and administered to the patient. The container of drug may hold the drug in a dry state and be combined, prior to use, with water or other liquid held in a separate container in order to minimize the deterioration of drug subject to such in the presence of water or other solvent or carrier. Stirring, mixing and/or low frequency vibration devices may be used to dissolve or disperse the dry drug in the liquid carrier or solvent. The tape-like connecting means preferably includes indices thereon which can be read directly by the patient or with the aid of a dispensing device to provide information such as the number of containers used and the number of unused containers remaining in a cassette. The tape-like structure of the disposable package is preferably loaded into the cassette in a folded configuration. The dispensing device is a hand-held, self-contained, portable device comprised of a means for removing covers from the porous membrane of each package (when needed, combining liquid from another container) and automatically dispersing the formulation from individual containers, preferably in response to a signal obtained as a result of measuring the inspiratory flow of a patient. The device also compresses and disperses a volume of air along with formulation.

An object of the invention is to provide a disposable package comprised of a plurality of containers (optionally including an opening for dispersing a stream of air) and a porous membrane through which a liquid, flowable formulation is forced from a container and aerosolized.

Another object is to provide a cassette which holds a disposable package therein and which cassette includes a mouth piece which leads from an area above each porous membrane - the mouth piece being integral with the cassette and disposable therewith.

Another object is to provide such a package wherein the drug is held in one container in a dry state and combined with a liquid held in a companion container at a time immediately prior to aerosolizing the drug.

Another object of the invention is to provide a dispensing device comprised of a means for forcing air through one or more openings in the cassette, package or device and liquid flowable formulations through a porous membrane with cone shaped pores after a means for measuring the inspiratory flow of a patient determines a threshold point.

Another object is to provide a system for the intrapulmonary delivery of drug to a patient comprised of a cellular array of packages loaded into a cassette which cassette is to be loaded into a dispensing device designed to aerosolize drugs.

An advantage of the invention is that individual sterile containers, formulations and porous membranes are used for each administration of drug.

A feature of the invention is that drug can be aerosolized without the use of a low boiling point propellant and in particular without low boiling point halocarbons such as fluorocarbons.

Another feature is that by simultaneously dispersing air with aerosolized drug particles, the particles avoid collision for longer periods.

Another advantage of the invention is that the liquid drug solutions contained within the individual containers need not and preferably do not include preservatives and/or any type of bacteriostatic compounds in that the containers are originally packaged in a sterile form and preferably consist essentially of liquid drug alone or in combination with a liquid and excipient carrier and the contents of the individual containers are used completely upon opening.

Another advantage is that the system makes it possible to disperse aerosolized drug at a relatively low velocity as compared to the velocity of aerosols dispersed from conventional metered dose inhalers.

Another advantage is that drugs which are unstable in a liquid (e.g. aqueous) state can be stored in a dry state and combined with a liquid immediately prior to aerosolization.

Another feature of the present invention is that a wide range of different pharmaceutically active drugs (with an excipient carrier as needed to form a liquid formulation) can be packaged within the individual sterile containers.

Another feature of the invention is that the individual containers of the package include one or more openings through which air can be forced, which openings are in close proximity to a thin membrane having cone shaped pores of substantially uniform diameter at their narrowest point in the range of about 0.25 micron to 6 microns.

Another feature of the invention is that the containers have channels leading therefrom to the porous membranes so that a vibrating mechanism in the cassette can be positioned directly below the porous membrane.

Yet another feature of the present invention is that the dispensing device or cassette includes a vibrator or high frequency signal generation device which vibrates the liquid being forced through the porous membrane of the package at different frequencies in a manner so as to promote regular sizing of the droplets from the stream forced from an opening and create an aerosol having uniform (or if desired a range of different) particle size in the range of 0.5 micron to 12 microns in diameter.

Another object of the present invention is to provide a disposable package comprised of a container for holding a liquid aerosolizable formulation, which container is connected via one or more channels to a chamber or resonance cavity positioned directly below a porous membrane such that when formulation from a container is forced through the channel into the resonance cavity and out of the pores of the membrane, the formulation will be aerosolized into particles having a diameter in the range of 0.5 micron to 12 microns.

Another advantage of the present invention is that the system including the device and disposable cassette is a hand-held, easily portable and usable device.

Another feature of the invention is that the package may include indices thereon in the form of visually readable numbers or letters which can be readily perceived by the user whether a dose has been delivered for a particular day and/or time of day and/or indicate the number of doses in the cassette which have been used and the number which remain for use.

Still another feature of the invention is to provide, in the cassette, a power source such as a battery in connection with indices on the package which are in the form of magnetic, optical and/or electronic records which can be read by the drug dispensing device which in turn presents a visual display to the user providing information on the amounts and times of doses released (in total or from a given cassette) and/or to be released.

Another feature is to provide a battery integral with the disposable cassette, which battery provides sufficient energy to power the device, including providing power to control the microprocessor, vibration the device, and piston or bellows to force formulation through the membranes and thereby create an aerosol from all of the liquid and/or suspension material contained within all of the containers present in that cassette.

It is another object of this invention to provide a pocket-sized, single, integrated device for recording the date, time and amount of aerosolized drug delivered at each drug delivery event which device is also capable of monitoring pulmonary function and maintaining a record of the date, time and value of each objective lung function and recording the information on a package.

It is another object of this invention to provide a device capable of monitoring and recording objective pulmonary function information and displaying such information in a manner integrated with drug dosing event information so as to provide a means of evaluating quantitative, objective measures of pulmonary function in the context of actual administered therapy.

It is another object of this invention to show that the evaluation of pulmonary function in light of actual patient compliance only has meaning if drug dosing events are actually associated with patient inspiration and firing of the aerosolized drug into the patient's mouth.

It is another object of this invention to show that interpretation of pulmonary function data in the context of actual drug dosing events allows physicians to counsel patients accurately with regard to avoidance of overdosing of potentially toxic inhaled aerosolized drugs such as bronchodilators and gives physicians a tool for quantitatively advising patients regarding adjustments to their long-term, anti-inflammatory, aerosolized drug treatment program and/or long term enzyme treatment program.

These and other objects, advantages and features of the present invention will become apparent to those persons skilled in the art upon reading the present disclosure and reviewing the figures forming a part hereof wherein like numerals refer to like components.

DETAILED DESCRIPTION OF PREFERRED EMBODIMENTS

Figure 1:
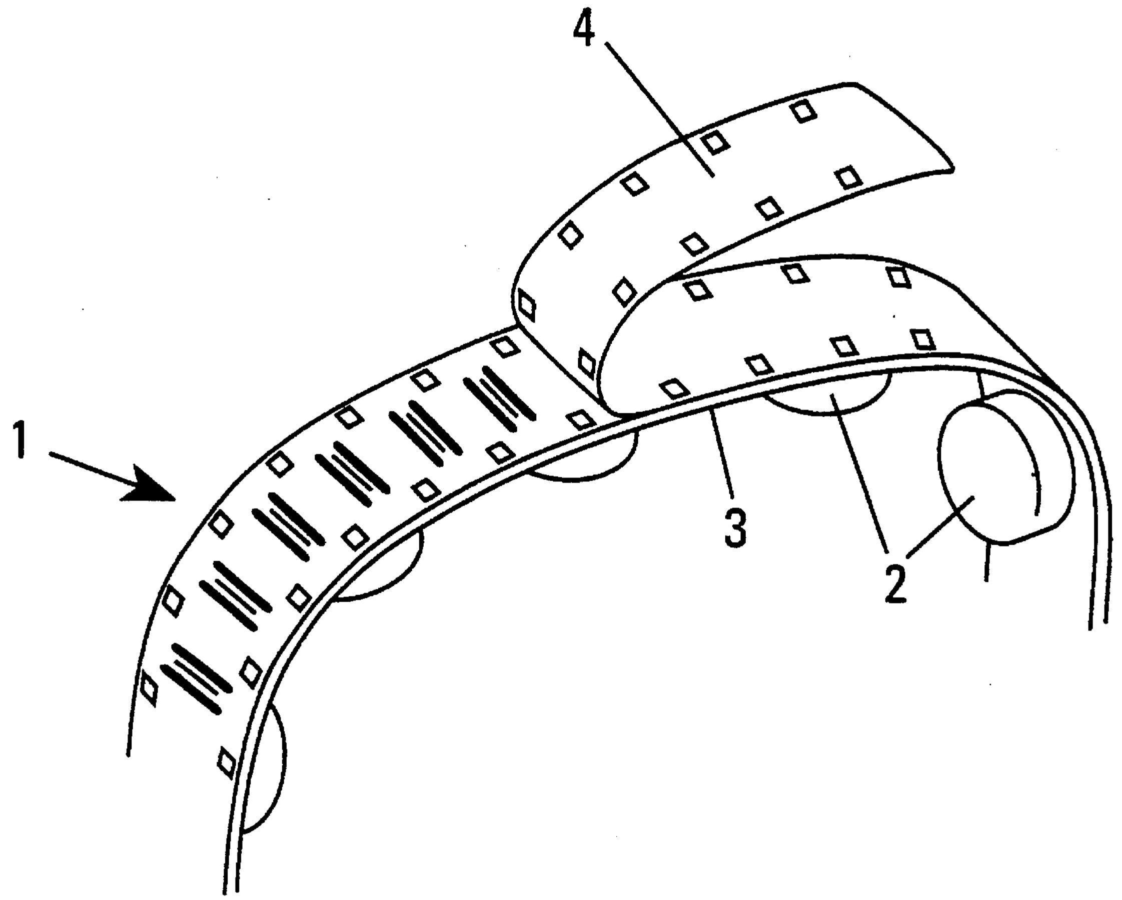
FIG. 1 is a perspective view of a disposable package of the present invention.

Before the disposable packages, devices, systems and methodology of the present invention are described, it is to be understood that this invention is not limited to the particular packages, devices, systems, components, formulations and methodology described, as such may, of course, vary. It is also to be understood that the terminology used herein is with the purpose of describing particular embodiments only, and is not intended to limit the scope of the present invention which will be limited only by the appended claims.

It must be noted that as used herein and in the appended claims, the singular forms "a," "and," and "the" include plural referents unless the context clearly dictates otherwise. Thus, for example, reference to "a formulation" includes mixtures of different formulations and reference to "the method of treatment" includes reference to equivalent steps and methods known to those skilled in the art, and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described. All publications mentioned herein are incorporated herein by reference to describe and disclose specific information for which the reference was cited in connection with.

Definitions

The terms "package" and "disposable package" are used interchangeably herein and shall be interpreted to mean a container or two or more containers linked together by an interconnecting means wherein each container preferably includes one or more channels which provide for fluid connection from the container to a porous membrane preferably not positioned directly over the container, and wherein each container includes at least one surface which is collapsible in a manner so as to allow the forced displacement of the contents of the container through a channel and out of the porous membrane (without rupturing the container) in a manner such that the contents is aerosolized. The disposable package preferably includes one or more openings near the porous membrane through which air can be forced or can be positioned alongside of air dispersion vents in a cassette or drug dispensing device described below. There are two variations of the package, depending on whether the drug can be stably stored in a liquid form or must be stored dry and combined with liquid immediately prior to aerosolization.

The contents of each container preferably consists essentially of a liquid, flowable formulation which includes a pharmaceutically active drug and (if the drug is not liquid and of a sufficiently low viscosity to allow the drug to be aerosolized) an excipient carrier, i.e. preferably without any additional material such as preservatives which might affect the patient. The formulation is a liquid, flowable formulation with a relatively low viscosity that can be readily aerosolized and is more preferably a flowable, liquid formulation consisting essentially of a pharmaceutically active drug dissolved or dispersed in an excipient carrier. When the contents must be stored in a dry state, the package further includes another container which holds the liquid and can be combined with the dry drug immediately prior to administration.

The term "cassette" shall be interpreted to mean a container which holds, in a protective cover, a package or a plurality of packages which packages are interconnected to each other and held in the cassette in an organized manner, e.g. interfolding or wound. The cassette is connectable to a dispensing device and preferably includes a power source, e.g. one or more batteries in the cassette which provide power to the dispensing device. The cassette may include air dispersion vents through which air can be forced when formulation is forced through the porous membranes.

The term "dosing event" shall be interpreted to mean the administration of a pharmaceutically active drug to a patient in need thereof by the intrapulmonary route of administration which event may encompass the release of drug contained within one or more containers. Accordingly, a dosing event may include the release of drug contained within one of many containers of the package held in a cassette or the drug contained within a plurality of such containers when the containers are administered at about the same time (e.g., within 10 minutes of each other, preferably within 1–2 minutes of each other). A dosing event is not interrupted by a monitoring event which would indicate, if followed by further drug delivery, the beginning of a new dosing event.

The terms "monitoring event" and "measuring" are used interchangeably herein and shall be interpreted to mean an event taking place prior to a "dosing event" whereby the inspiratory flow of the patient's inhalation is measured in order to determine the optimal cumulative volume and inspiratory flow at which to actuate the firing of a mechanism such as a roller or piston which causes the collapse of a container wall forcing the drug from the container in a manner such that the drug is aerosolized. It is preferable to carry out a "monitoring event" immediately prior to (within two minutes or less) each "dosing event" so as to optimize the ability to repeatedly deliver the same amount of drug to the patient at each dosing event. It is also preferable to continue to monitor inspiratory flow during any drug delivery and to record inspiratory flow before, during and after the release of drug.

The term "inspiratory flow" shall be interpreted to mean a value of air flow calculated based on the speed of the air passing a given point along with the volume of the air passing that point with the volume calculation being based on integration of the flow rate data and assuming atmospheric pressure and temperature in the range of about 10° C. to about 35° C.

The term "inspiratory flow profile" shall be interpreted to mean data calculated in one or more monitoring events measuring inspiratory flow and cumulative volume, which profile can be used to determine a point within a patient's inspiratory cycle which is optimal for the release of drug to be delivered to a patient. It is emphasized that the optimal point within the inspiratory cycle for the release of drug is not calculated based on a point within the cycle likely to result in the maximum delivery of drug but rather a point in the cycle most likely to result in the delivery of the reproducible amount of drug to the patient at each release of drug, i.e. repeatability of the amount delivered is important, not maximizing the amount delivered.

The term "respiratory drug" shall be interpreted to mean any pharmaceutically effective compound used in the treatment of any respiratory disease and in particular the treatment of diseases such as asthma, bronchitis, emphysema and cystic fibrosis. Useful "respiratory drugs" include those which are listed within the Physician's Desk Reference (most recent edition). Such drugs include beta adrenergics which include bronchodilators including albuterol, isoproterenol sulfate, metaproterenol sulfate, terbutaline sulfate, pirbuterol acetate and salmeterol formotorol; steroids including beclamethasone dipropionate, flunisolide, fluticasone, budesonide and triamcinolone acetonide. Anti-inflammatory drugs used in connection with the treatment of respiratory diseases include steroids such as beclamethasone dipropionate, triamcinolone acetonide, flunisolide and fluticasone. Other anti-inflammatory drugs include cromoglycates such as cromolyn sodium. Other respiratory drugs which would qualify as bronchodilators include anticholenergics including ipratropium bromide. The present invention is intended to encompass the free acids, free bases, salts, amines and various hydrate forms including semi-hydrate forms of such respiratory drugs and is particularly directed towards pharmaceutically acceptable formulations of such drugs which are formulated in combination with pharmaceutically acceptable excipient materials generally known to those skilled in the art - preferably without other additives such as preservatives. Preferred drug formulations do not include additional components which have a significant effect on the overall formulation such as preservatives. Thus preferred formulations consist essentially of pharmaceutically active drug and a pharmaceutically acceptable carrier. However, if a drug is liquid without an excipient the formulation may consist essentially of the drug which has a sufficiently low viscosity that it can be aerosolized using a dispenser of the present invention.

The term "therapeutic index" refers to the therapeutic index of a drug defined as $LD_{50}/ED_{50}$. The $LD_{50}$ (lethal dose, 50%) is defined as the dose of a drug which kills 50% of the animals, and the $ED_{50}$ is defined as the effective dose of the drug for 50% of the individuals treated. Drugs with a therapeutic index near unity (i.e. $LD_{50}/ED_{50}$ is approximately equal to 1) achieve their therapeutic effect at doses very close to the toxic level and as such have a narrow therapeutic window, i.e. a narrow dose range over which they may be administered.

The terms "formulation" and "liquid formulation" and the like are used interchangeably herein to describe any pharmaceutically active drug by itself or with a pharmaceutically acceptable carrier in flowable liquid form. Such formulations are preferably solutions, e.g. aqueous solutions, ethanolic solutions, aqueous/ethanolic solutions, saline solutions and colloidal suspensions.

The terms "lung function" and "pulmonary function" are used interchangeably and shall be interpreted to mean physically measurable operations of a lung including but not limited to (1) inspiratory and (2) expiratory flow rates as well as (3) total lung volume. Methods of quantitatively determining pulmonary function are used to measure lung function. Quantitative determination of pulmonary function is important because lung disease is typically associated with deteriorating pulmonary function. Methods of measuring pulmonary function most commonly employed in clinical practice involve timed measurement of inspiratory and expiratory maneuvers to measure specific parameters. For example, forced vital capacity (FVC) measures the total volume in liters exhaled by a patient forcefully from a deep initial inspiration. This parameter, when evaluated in conjunction with the forced expired volume in one second ($FEV_1$), allows bronchoconstriction to be quantitatively evaluated. A problem with forced vital capacity determination is that the forced vital capacity maneuver (i.e. forced exhalation from maximum inspiration to maximum expiration) is largely technique dependent. In other words, a given patient may produce different FVC values during a sequence of consecutive FVC maneuvers. The FEF 25–75 or forced expiratory flow determined over the mid-portion of a forced exhalation maneuver tends to be less technique dependent than the FVC. Similarly, the $FEV_1$ tends to be less technique dependent than FVC. In addition to measuring volumes of exhaled air as indices of pulmonary function, the flow in liters per minute measured over differing portions of the expiratory cycle can be useful in determining the status of a patient's pulmonary function. In particular, the peak expiratory flow, taken as the highest air flow rate in liters per minute during a forced maximal exhalation, is well correlated with overall pulmonary function in a patient with asthma and other respiratory diseases. The present invention carries out treatment by administering drug in a drug delivery event and monitoring lung function in a monitoring event. A series of events are carried out over time to determine if lung function is improved.

Each of the parameters discussed above is measured during quantitative spirometry. A patient's individual performance can be compared against his personal best data, individual indices can be compared with each other for an individual patient (e.g. $FEV_1$ divided by FVC, producing a dimensionless index useful in assessing the severity of acute asthma symptoms), or each of these indices can be compared against an expected value. Expected values for indices derived from quantitative spirometry are calculated as a function of the patient's sex, height, weight and age. For instance, standards exist for the calculation of expected indices and these are frequently reported along with the actual parameters derived for an individual patient during a monitoring event such as a quantitative spirometry test.

The term "respiratory disease" shall be interpreted to mean any pulmonary disease or impairment of lung function. Such diseases include restrictive and obstructive disease and diseases such as emphysema which involve abnormal distension of the lung frequently accompanied by impairment of heart action. Restrictive diseases tend to limit the total volume of air that a patient is able to exchange through inspiration and expiration. Restrictive disease, such as can be present in certain types of fibrotic processes, can therefore be detected by reduced FVC indices. Obstructive disease, such as is present in patients with asthma, tends not to affect the total volume of air exchangeable through inspiration and expiration but rather the amount of time required for forced exhalation of air. In particular, the $FEV_1$ is markedly reduced in patients with acute asthma symptoms. More specifically, the $FEV_1$, when taken as a ratio of FVC (i.e. $FEV_1$ divided by FVC), is markedly reduced in patients with acute asthma. In addition to increasing the amount of time required for a full forced expiration, the presence of acute bronchoconstrictive disease tends to decrease the peak expiratory flow measured over a typical forced exhalation.

The term "porous membrane" shall be interpreted to mean a membrane of material in the shape of a sheet having any given outer parameter shape, but preferably in the form of an elongated rectangle, wherein the sheet has a plurality of openings therein, which openings may be placed in a regular or irregular pattern, and which openings have a diameter in the range of 0.25 micron to 6 microns and a pore density in the range of $1\times10^4$ to about $1\times10^8$ pores per square centimeter. The membrane is preferably comprised of a material having a density in the range of 0.25 to 3.0 $mg/cm^2$, more preferably 1.7 $mg/cm^2$, and a thickness of about 2 to about 20 microns, more preferably 8 to 12 microns. The membrane material is preferably hydrophobic and includes materials such as polycarbonates and polyesters which may have the pores formed therein by any suitable method including anisotropic etching or by etching through a thin film of metal or other suitable material. The membrane material, preferably have pores with a conical configuration and have sufficient structural integrity so that it is maintained intact (will not rupture) when subjected to force in the amount of about 20 to 200 psi while the formulation is forced through the pores.

General Description

The present invention provides a non-invasive means of delivering any type of drug to a patient by the intrapulmonary route. The devices and methodology used do not require the release of low boiling point propellants in order to aerosolize drug which propellants are conventionally used in connection with hand-held metered dose inhalers. However, like conventional hand-held metered dose inhalers the devices of the present invention are hand-held, self-contained, highly portable devices which provide a convenient means of delivering drugs to a patient via the intrapulmonary route.

The liquid, flowable formulations of the present invention may include preservatives or bacteriostatic type compounds. However, the formulation preferably consists essentially of pharmaceutically active drug and pharmaceutically acceptable carrier. The formulation may consist essentially of the drug (i.e. without carrier) if the drug is freely flowable and can be aerosolized. Useful formulations may consist essentially of formulations currently approved for use with nebulizers. However, nebulizer formulations must, in general, be diluted prior to administration. The formulations are sterilized and placed in individual containers in a sterile environment. Further, since preferred embodiments of the devices used in connection with the present invention include a means of analyzing breath flow and a microprocessor capable of making calculations based on the inhalation profile, the present invention can provide a means for repeatedly (1) dispensing and (2) delivering the same amount of drug to a patient at each dosing event.

The present invention includes at least four distinct aspects which include (1) a disposable package, (2) a cassette which includes a plurality of packages, (3) a drug dispensing device which can be loaded with a cassette, and (4) a method of drug delivery.

Referring now to the figures the details of the structure and operation of the various aspects of the invention can be described in detail. FIG. 1 provides a prospective view of a disposable package 1 which includes a plurality of substantially identical containers 2 each of which holds a pharmaceutically active drug by itself or in combination with an excipient carrier. The containers 2 are each interconnected with each other by an interconnecting tape 3 and the tape 3 is covered by a cover 4.

Figure 2:
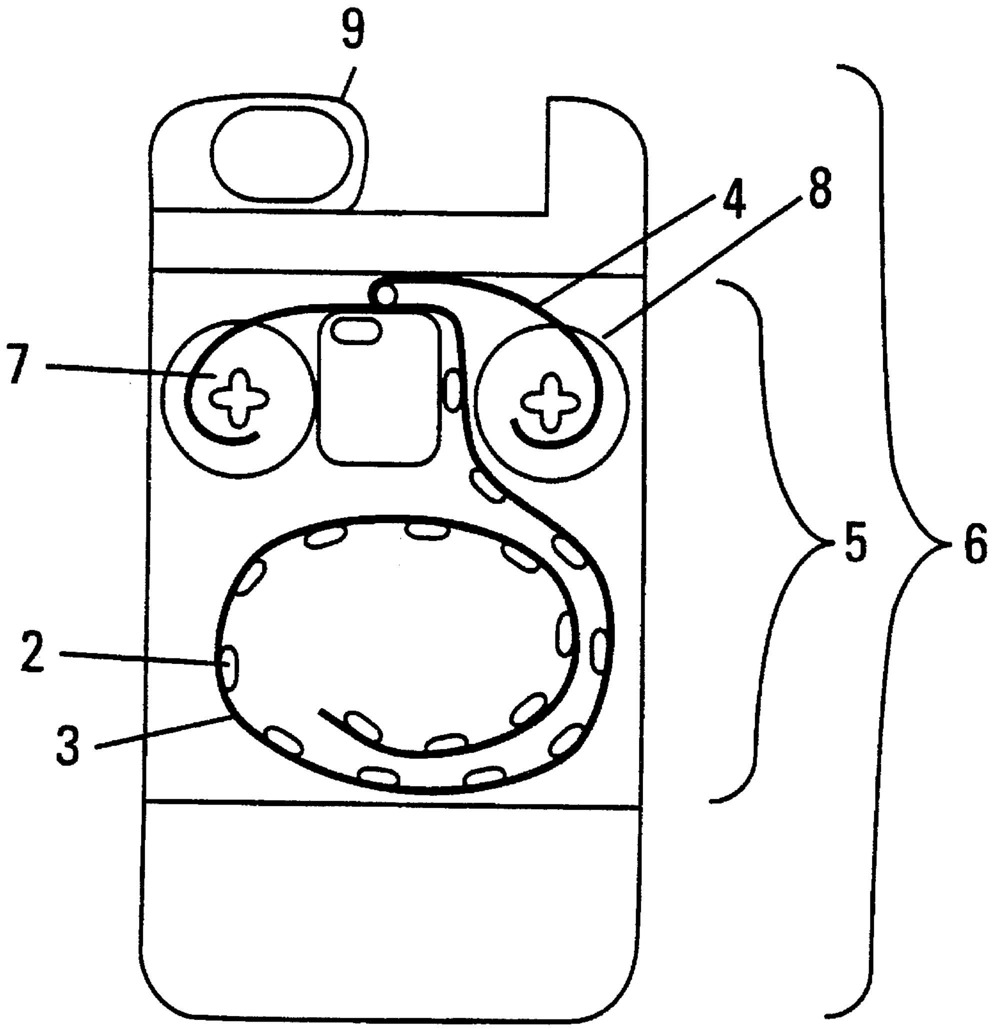
FIG. 2 is a cross-sectional view of a drug dispensing device of the invention.

Referring to FIG. 2 which is a cross-sectional view of the cassette 5 loaded into a drug delivery device 6 makes it possible to describe the operation of the disposable package 1 within the cassette 5 and the device 6. In essence, the disposable package 1 is folded or wound into the cassette in a manner which makes it possible to move the individual containers 2 into a drug release position within the device 6. While the containers 2 are moved into position the cover 4 is removed. Although it is possible to rewind any used portion of the package on a sprocket 7 and rewind the used cover 4 on a sprocket 8 or randomly fold it into a compartment it is also possible to disperse the used portion outside of the cassette 5 and device 6 and immediately dispose of such.

Although the device 6 shown in FIG. 2 includes a mouthpiece 9 shown here as rotatably attached thereon, it is possible to reconfigure the components so that the mouthpiece 9 is part of and integral with the cassette 5. This arrangement of components makes it possible to dispose of the mouthpiece with the cassette 5 when all the containers 2 on the package 1 have been emptied.

In essence, the device 6 operates by having the user patient inhale from the mouthpiece 9. Components of the device described further below make it possible to determine an inhalation profile based on the particular users lung capacity and function. The microprocessor within the device calculates a point within the inhalation profile at which it would be most desirable to release drug in order to maximize the repeatability of the amount of drug delivered to the patient. At this point, a mechanical device such as a piston (described below) is released and applies force against a container 2. The drug within the container is ultimately aerosolized and delivered to the patient. The details of how drug leaves each container 2 and ultimately leaves the mouthpiece 9 are described in detail below.

Figure 3:
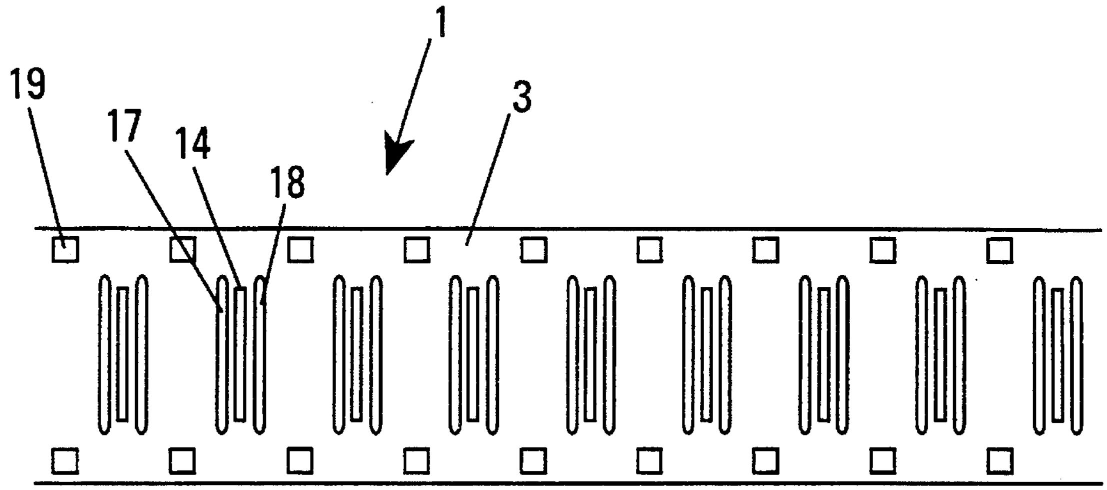
FIG. 3 is a top plan view of a disposable package of the invention.
Figure 4:
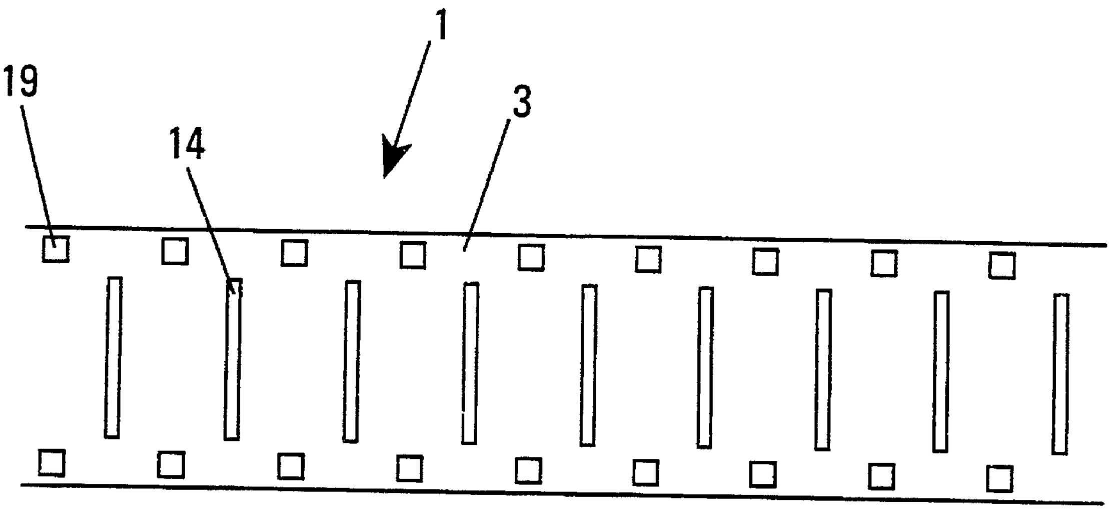
FIG. 4 is a top plan view of another embodiment of a disposable package of the invention.
Figure 5:
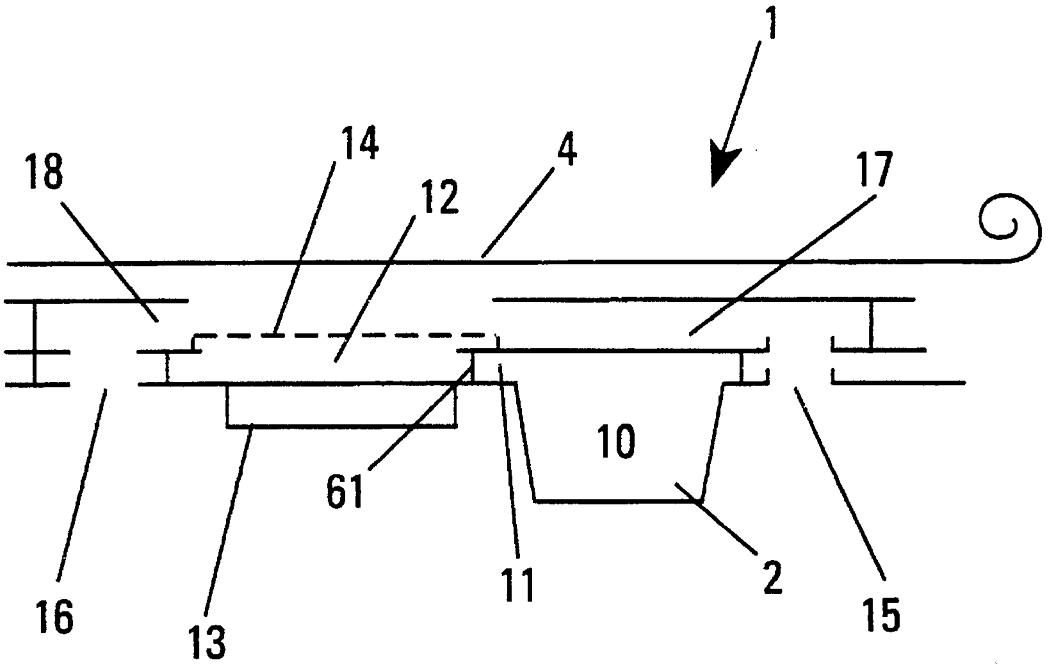
FIG. 5 is a cross-sectional view of a portion of a disposable package of the present invention.
Figure 6:
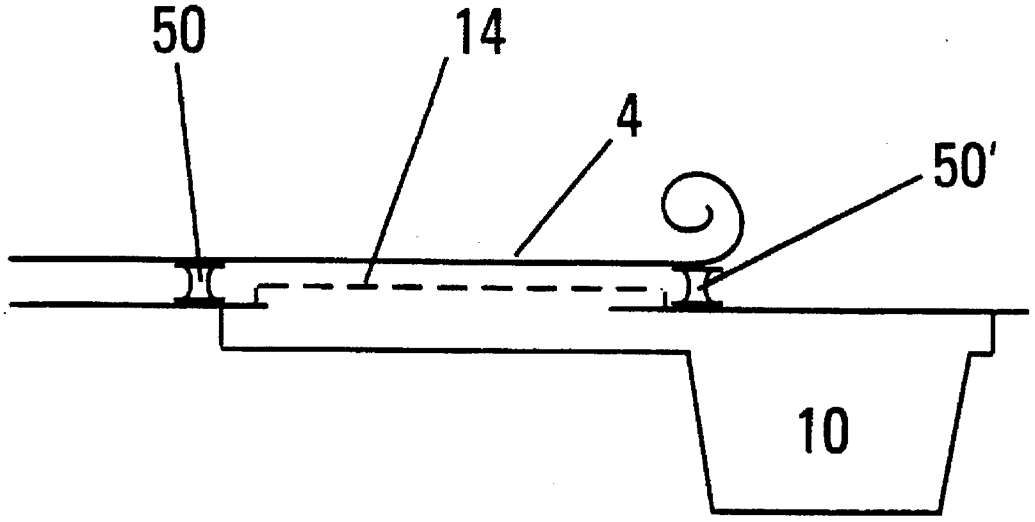
FIG. 6 is a cross-sectional view of a portion of another embodiment of a disposable package of the present invention.
Figure 7:
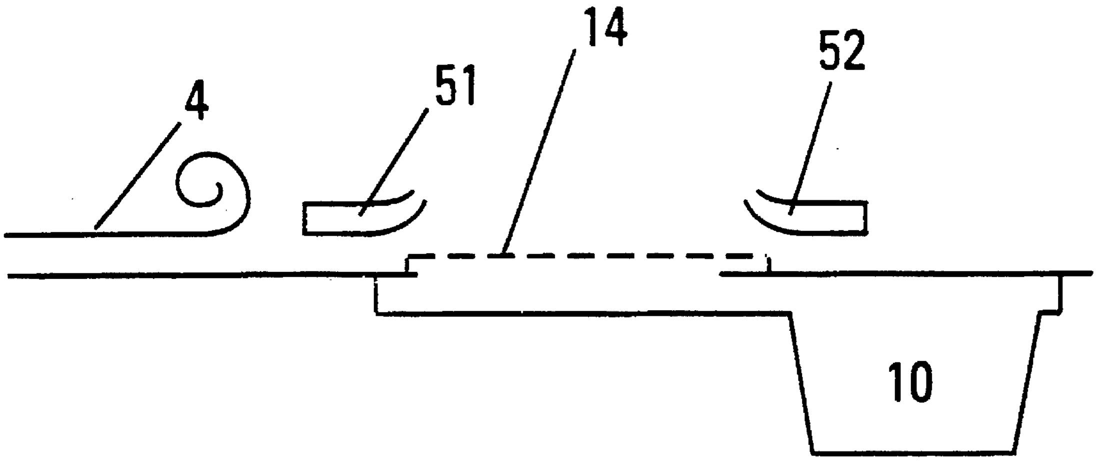
FIG. 7 is a cross-sectional view of a portion of a disposable package and air dispersion vents of the invention.

FIG. 3 is a top view of a package as shown in FIG. 5, and FIG. 4 is a top view of a package as shown in FIG. 6. In FIG. 3, openings 17 and 18 are shown on either side of the porous membrane 14. Air can pass out of the openings 17 and 18. However, FIG. 4 does not include any such air vent openings. The package as shown in FIGS. 4 and 6 can operate without air flow. However, it is preferable to include air dispersion vents 51 as shown in FIG. 7, which vents may be part of the cassette or the device. The precise procedures for creating an aerosol using the package are described further below.

FIG. 5 is a cross-sectional view of the package 1 which is shown in FIG. 1. A drug formulation 10 is contained within the container 2. When pressure is applied to the container 2 such as by the force provided from a piston the container 2 is collapsed and the formulation 10 within the container 2 is forced out through a channel 11. A rupturable barrier 61 is preferably in the channel 11 to prevent bacterial contamination of the drug in the container 2. The barrier 61 is broken upon the application of force of 25 psi or less. The channel 11 leads to a resonance cavity 12. The cavity 12 is positioned above a vibrating device 13 which may be a piezoelectric vibrating device. Any mechanism capable of creating vibrations in the range of from about 800 kilohertz to about 4,000 kilohertz can be used. The device is preferable capable of varying the frequency to create different sized particles. Further, the device is preferably low cost such as a sheet of poly (vinylidene fluoride) film an example of which is sold as Kynar® by Pennwalt Corporation, Valley Forge, Pa. (U.S.A.). From the cavity 12 formulation is forced (by pressure created from collapsing the container 2) through pores within a porous membrane 14 which covers the upper surface of the cavity 12.

FIG. 6 is a cross-sectional view of a simpler embodiment of the package shown in FIG. 5. Specifically, the package of FIG. 6 includes the container 2 which holds the formulation 10 and provides for a channel 11 through which the formulation can pass into the cavity 12 which is positioned below the porous membrane 14. The cover 4 is held in place by one or more seals 50 and 50'. The seals may be comprised of glue or other suitable materials using suitable sealing techniques which make it possible to place the cover 4 over the porous membrane and thereafter remove the cover without damaging the porous membrane or other components of the package.

It is possible to use a package as shown in FIG. 6 without the use of additional air flow such as the air flow coming out of the air vents 17 and 18 as shown in FIGS. 3 and 5. However, it is preferable to use a package as shown in FIG. 6 in combination with air dispersion vents 51 and 52 as shown in FIG. 7. The vents 51 and 52 are either part of and integral with the cassette 5 or the device 6 as shown in FIG. 2. The air vents 51 and 52 have openings which are positioned such that, when air is forced through the vents, it exits in the general direction of the particles exiting from the porous membrane 14. Accordingly, the air causes the particles to move along in the same direction, and aids in preventing the collision and thereafter aggregation of particles.

Figure 8:
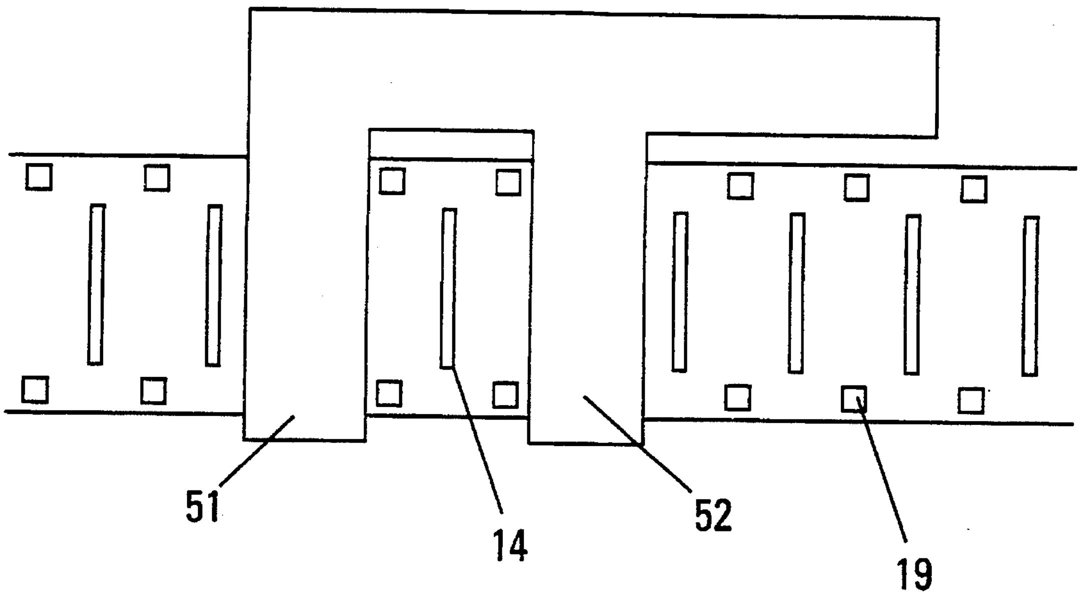
FIG. 8 is a top plan view of a disposable package of the invention and air dispersion vents.

FIG. 8 is a top view of an embodiment as shown in FIG. 7. The device 6 includes a system for forcing compressed air into the air dispersion vents 51 and 52 on the device or cassette so that it exits in substantially the same direction as the particles exiting from the porous membrane 14. The compressed air being forced out of the vents 51 and 52 can be derived from any suitable source, including a container of compressed air (not shown). However, it is preferable to create the compressed air by using a mechanical device to be operated by the user. For example, a spring-loaded piston or bellows within a cylinder can be cocked by compressing the spring which, upon release, allows the piston to move through the cylinder and force air outward into the vents 51 and 52.

The porous membrane 14 includes pores which have a diameter in the range of about 0.25 micron to about 6 microns and a pore density in the range of $1\times10^4$ to about $1\times10^8$ pores per square centimeter. The porous membrane 14 is preferably comprised of a material having a density in the range of about 0.25 to 3.0 $mg/cm^2$, more preferably about 1.7 $mg/cm^2$, and a thickness of about 2 to about 20 microns, more preferably 8 to 12 microns. The membrane 14 is preferably comprised of a hydrophobic material which includes materials such as polycarbonates and polyesters which have pores formed therein by anisatarpic etching or by etching through a thin film. The membrane material may include cylindrically shaped pores, pores which have a non-cylindrical shape and specifically pores which have a configuration such as an hour glass or conical configuration. A conical configuration is preferred with the narrowest point of the conical configuration having an opening with a diameter in the range of 0.2 micron to 6 microns. The material of the porous membrane has sufficient structural integrity so that it is maintained intact (will not rupture) when the material is subjected to force in the amount of about 20 to about 200 psi while formulation 10 is being forced through the pores of the membrane 14. As explained above with respect to FIG. 1 the protective cover layer 4 must be removed prior to release of drug.

In FIG. 5, the package 1 also includes openings 15 and 16 which may be positioned along either side of the porous membrane 14 or connected on either side of the membrane 14 via channels 17 and 18 respectively. One or more openings such as openings 15 and 16 are provided so that air can be forced through these openings and can exit the package 1 along with the formulation 10 being forced through the pores of the membrane 14. The air flow forced through the openings 15 and 16 is preferably maintained at a speed approximately equal to the speed of the formulation being forced through the pores of the membrane 14. The air flow is provided in order to aid in preventing particles of formulation 10 from colliding with each other and aggregating. Thus the object of the air flow is to keep the particles which escape from the pores in the membrane 14 separate from each other so that they maintain their small size and can be inhaled deeply into smaller channels within the lungs. However, the speed of the air forced through the openings 15 and 16 can be varied in order to create an aerosol dispersion wherein the particles have greater variation in size in that the speed is adjusted to allow some of the particles to collide with each other and therefore form particles which are twice, three times or four times etc. the mass of the smallest particles. Those skilled in the art will recognize that adjustments in the air flow can be made in order to obtain particle sizes of the desired size dispersion depending upon the particular disease being treated and results desired.

As indicated above the pores within the membrane 14 have a size in the range of about 0.25 to 6 microns. When the pores have this size the particles which escape through the pores to create the aerosol will have a diameter of approximately twice that size i.e. have a particle diameter in the range of 0.5 to 12 microns. The air flow for the openings 15 and 16 is intended to keep the particles within this size range. The creation of the small particles is greatly facilitated by the use of the vibration device 13 which is positioned below the cavity 12. The vibration device 13 provides a vibration frequency in the range of about 800 to about 4000 kilohertz. Those skilled in the art will recognize that some adjustments can be made in the pore size, vibration frequency, pressure, and other parameters based on the density and viscosity of the formulation 10 keeping in mind that the object is to provide aerosolized particles having a diameter in the range of about 0.5 to 12 microns.

The drug formulation is preferably in a low viscosity liquid formulation which is most preferably a formulation which can be aerosolized easily and includes respiratory drug formulations currently used in nebulizers. The viscosity of the drug by itself or in combination with a carrier must be sufficiently low that the formulation can be forced through the membrane 14 using 20 to 200 psi to form an aerosol preferably having a particle size in the range of about 0.5 to 12 microns.

The container 2 can be in any desired size. In most cases the size of the container is not directly related to the amount of drug being delivered in that most formulations include relatively large amounts of excipient material e.g. water or a saline solution. Accordingly, a given size container could include a wide range of different doses by varying drug concentration. The amount of drug delivered to the patient will vary greatly depending on the particular drug being delivered. In accordance with the present invention it is possible to deliver a wide range of different drugs. For example, the drugs included within the container 2 could be drugs which have a systemic effect such as narcotic drugs, for example fentanyl, sufentanil, or anxiolytic drugs such as diazepam and midazolam. In addition, mixed agonist/antagonist drugs such as butorphanol can also be used for the management of pain delivered to provide relief from pain or anxiety. However, in that the drugs are delivered directly to the lungs, respiratory drugs are included and include proteins such as DNAse. The preferred respiratory drugs are albuterol, beclamethasone dipropionate, triamcinolone acetonide, flunisolide, cromolyn sodium, and ipratropium bromide, and include, free acids, bases, salts and various hydrate forms thereof generally administered to a patient in an amount in the range of about 50 μg–10,000 μg. These doses are based on the assumption that when intrapulmonary delivery methodology is used the efficiency of the delivery is approximately 10% and adjustments in the amount released must be made in order to take into account the efficiency of the device. The differential between the amount of respiratory drug actually released from the device and the amount of respiratory drug actually delivered to the patient varies due to a number of factors. In general, the present device is approximately 20% efficient, however, the efficiency can be as low as 10% and as high as 50% meaning that as little as 10% of the released respiratory drug may actually reach the lungs of the patient and as much as 50% might be delivered. The efficiency of the delivery will vary somewhat from patient to patient and must be taken into account when programming the device for the release of respiratory drug. In general, a conventional metered dose inhaling device is about 10% efficient.

Referring to FIG. 2, the interconnecting tape 3 is designed so that the package 1 can be readily integrated with and moved through the cassette 5 in the drug dispensing device 6. The package 1 may also include indices which are positioned on individual containers 2 or the interconnecting tape 3. The indices may be electronic and may be connected to a power source such as a battery. When the indices are in the form of visually perceivable numbers, letters or any type of symbol capable of conveying information to the patient using the device. Alternatively, the indices may be connected to a power source such as a battery when the indices are in the form of magnetically, optically or electronically recorded information which can be read by the drug dispensing device 6 which in turn provides visual or audio information to the user. The indices can be designed for any desired purpose but in general provides specific information relating to the day and/or time which the drug within a container should be administered to the patient. Such indices may record, store and transfer information to the dispensing device 6 regarding the number of containers 2 remaining in the cassette 5, the number of containers 2 used and/or the specific drug 10, and amount of drug 10 present in each container 2.

If the user is to take the drug once a day then each container may be labeled with a day of the week. However, if the user is to take the drug more than once a day such as four times a day then only one row of containers is labeled with the days of the week whereas the other rows within a column of four are labeled with different times of the day e.g. 6:00 a.m., 12:00 p.m., 6:00 p.m., 12:00 a.m. The labeling can be in any format and could include days of the month or other symbols or numbers in any variation or language.

In addition to disclosing specific information regarding the day and time for drug delivery the indices could provide more detailed information such as the amount of drug dispensed from each container which might be particularly useful if the containers included different amounts of drug. Further, magnetic, optical and/or electronic indices could have new information recorded onto them which information could be placed there by the drug dispensing device. For example, a magnetic recording means could receive information from the drug dispensing device indicating the precise time which the drug was actually administered to the patient. In addition to recording the time of delivery the device could monitor the expected efficacy of the delivery based on factors such as the inspiratory flow rate which occurred following the initial release of drug. The information recorded on the array could then be read by a separate device, interpreted by the care-giver and used to determine the usefulness of the present treatment methodology. For example, if the patient did not appear to be responding well but the recorded information indicating that the patient had taken the drug at the wrong time or that the patient had misdelivered drug by changing inspiratory flow rate after initial release it might be determined that further education in patient use of the device was needed but that the present dosing methodology might well be useful. However, if the recordings indicated that the patient had delivered the drug at the proper time using the proper techniques and still not obtained the correct results a different drug or dosing methodology might be recommended.

The containers 2 on the package 1 are also referred to as drug dosage units. Each container 2 includes at least one wall which can be collapsed to allow liquid contents 10 present in the container to be forced out of the pores of the membrane 14. In accordance with one embodiment the container 2 has cylindrical walls with bellows or accordion-like undulations so that the bottom of the container 2 can be forced upward towards the top of the container and allow liquid 10 present within the container 2 to be forced out of a plurality of pores in membrane 14.

Dual Compartment Package

The packages as shown within FIGS. 5 and 6 can be used in connection with nearly all drugs in that nearly all pharmaceutically active drugs can be dissolved in an excipient such as water, saline solution, ethanol, or combinations thereof in order to provide the desired formulation which can be expelled out of the membrane 14. However, some pharmaceutically active drugs must be maintained in a dry state in that the drugs are subject to deterioration such as hydrolysis in the presence of water. Due to the need to have drugs in a form which is not substantially deteriorated from their original form, it is necessary to package such drugs in a dual compartment system.

Figure 10:
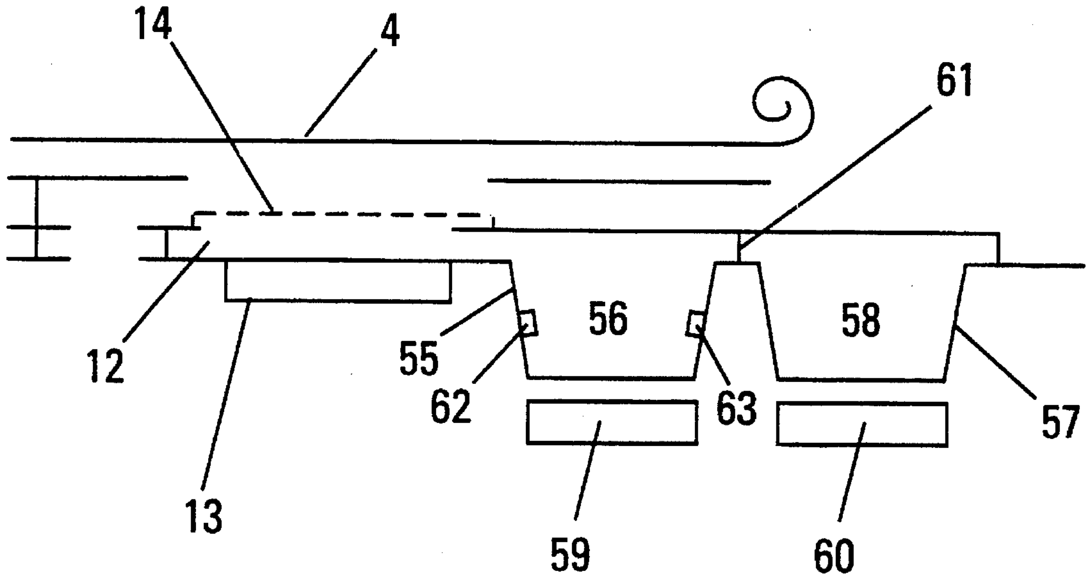
FIG. 10 is a cross-sectional plan view of a disposable package with dual containers.

A dual system package is shown in FIG. 10. The package includes the same components of the package shown in FIG. 5, such as the cover 4 and porous membrane 14. However, the drug-containing container is the container 55, which includes a powdered or dry form of a drug 56. The container 55 is positioned below a piston 59 or other device for collapsing the container 55. A separate container 57 includes a liquid 58 which can be combined with the powder 56 in order to form a solution or a dispersion. In order to use the package, a piston 60 or other device is used to collapse the container 57 and force the contents 58 outward through a breakable seal 61 positioned between the containers 55 and 57.

After the liquid 58 enters into the container 55, it is mixed with the dry powder 56 using mixing components 62 and 63, which may be vibrating devices, ultrasonic devices, or other suitable mechanisms allowing for the mixing of the liquid and dry components. After mixing has taken place, the piston 59 collapses the container 55, forcing the solution or suspension outward into the chamber 12 and through the porous membrane 14 after the removal of the cover 4.

In order to separate the liquid and the drug, it is also possible to include a single container with a first and second compartment. The first and second compartments are separate but are, at least in part, separated by a weakened wall or wall portion which can be ruptured upon the application of additional pressure such as by increasing the pressure within the second compartment by approximately 50% or more. The increased pressure is obtained by directing a mechanical means such as a roller, piston or blast of pressurized air against a collapsible wall of the second compartment. The collapsible wall and the remainder of the container must have sufficient structural integrity to be maintained intact (not rupture) while the contents are forced out, generally by the application of about 20 to 200 psi.

Particle Accumulation

As pointed out in connection with the description of the package of FIG. 5, air should be forced out of the package 1 along with the formulation 10 being forced out of the membrane 14. This can also be efficiently accomplished using a structural configuration as is shown in FIG. 6. A top view of the package 1 is shown in FIG. 3. The packages of FIGS. 5 and 6 are shown in top views, respectively, within FIGS. 3 and 4. The containers 2 are positioned below the package and are not shown in FIGS. 3 and 4. However, FIGS. 3 and 4 do show openings which can accommodate teeth, thereby providing a means for moving the package along within the cassette and the device. Although these openings 19 are shown within both embodiments, it is not necessary to include the openings, but it is preferable to include some means for moving the package along within the cassette and the device so that individual containers 2 can be brought into a firing position within the cassette and device and then moved out of position once the formulation within the container 2 has been expelled.

When the drug formulation 10 within a package 2 is forced out of the porous membrane 14, air is simultaneously forced out of the elongated openings 17 and 18 positioned on either side of each of the porous membrane openings 14. As formulation is forced out of the porous membrane 14, vibration is applied by means of the vibrating device 13 (shown in FIG. 4) so that the stream of formulation exiting each of the pores in the membrane 14 is broken up to form particles, which particles will have a diameter in the range of about 0.5 to 12 microns. In that the particles formed are very small, they can be substantially effected by the frictional resistance created from static air. Unless the air is moved along in the direction of the flow of the particles, the particles will quickly slow in speed and collide with one another and combine with one another, thereby forming larger particles. This particle collision followed by particle accumulation is not desirable in that the larger particles will not enter deeply into the lung tissue due to the small size of the channels within the lungs. In order to reduce particle collision and accumulation, air is forced from the openings 17 and 18 at a speed which is approximately equal to the speed of the particles being forced out of the pores of the membrane 14. When the air speed and particle speed are substantially equal, the particles do not undergo frictional resistance from the surrounding air and are not slowed and do not collide with one another - at least do not collide to the same extent they do when the air flow is not present.

Depending upon the end result required the rate and amount of air flow can be varied so as to allow for some collisions between some of the particles. When collisions occur the resulting aerosol is not a "monodisperse" aerosol wherein all the particles have substantially the same size. Collisions result in a "multi-disperse" aerosol wherein the particle sizes vary over a predetermined range. For example, the initial particles being dispersed from the porous membrane could have a size of approximately 2 microns in diameter. Some of these particles could be allowed to collide with other particles by adjusting the air flow so as to create particles of twice that volume and some of these particles could be allowed to collide with particles of the same size and particles of the original two micron diameter size thereby creating a multi-dispersed aerosol containing particles of a size of two microns in diameter, twice that volume, three times that volume and four times that volume, etc.

In order to obtain the maximum benefit of the air flow, it is desirable to have the porous membrane 14 in an elongated rectangular configuration and to have the openings 17 and 18 positioned close to the membrane opening 14 on either side of the membrane 14 with a similar configuration, i.e. elongated rectangle. The elongated rectangular configuration is desirable in that it is a configuration wherein a large amount of the particles being expelled from the membrane 14 are brought into contact with and thereby influenced by the air flow exiting from the openings 17 and 18. If the configuration of the opening of the membrane 14 were, for example, circular, the particles exiting near the center of the circular configuration would not be carried along by the air flow, and would therefore slow down due to resistance from the air and collide with one another.

Drug Delivery Device

A plan view of a simple embodiment of the drug delivery device 6 of the present invention is shown within FIGS. 4 and 5. Before describing the details of the individual components of the device 6, a general description of the device and its operation as distinguished from prior art devices is in order.

As indicated in the background of the invention, conventional metered dose inhalers and nebulizers suffer from a number of disadvantages. These disadvantages result in the inability to use these devices to repeatedly deliver the same amount of drug to a patient. In part, this results from the fact that users of such devices actuate the release of the drug by pushing a button which opens a valve causing drug to be released. Such methodology is not desirable because the patient will often actuate drug release at the wrong point within the inspiratory cycle. The drug dispensing device of the present invention preferably includes electronic and mechanical components which eliminate direct user actuation of drug release. More specifically, the device preferably includes a means for measuring inspiratory flow and sending an electrical signal as a result of the measurement and also preferably includes a microprocessor which is programmed to receive, process, analyze and store the electrical signal of the means for measuring flow and upon receipt of signal values within appropriate limits sending an actuation signal to the mechanical means which causes drug to be extruded from the pores of the porous membrane.

Figure 9:
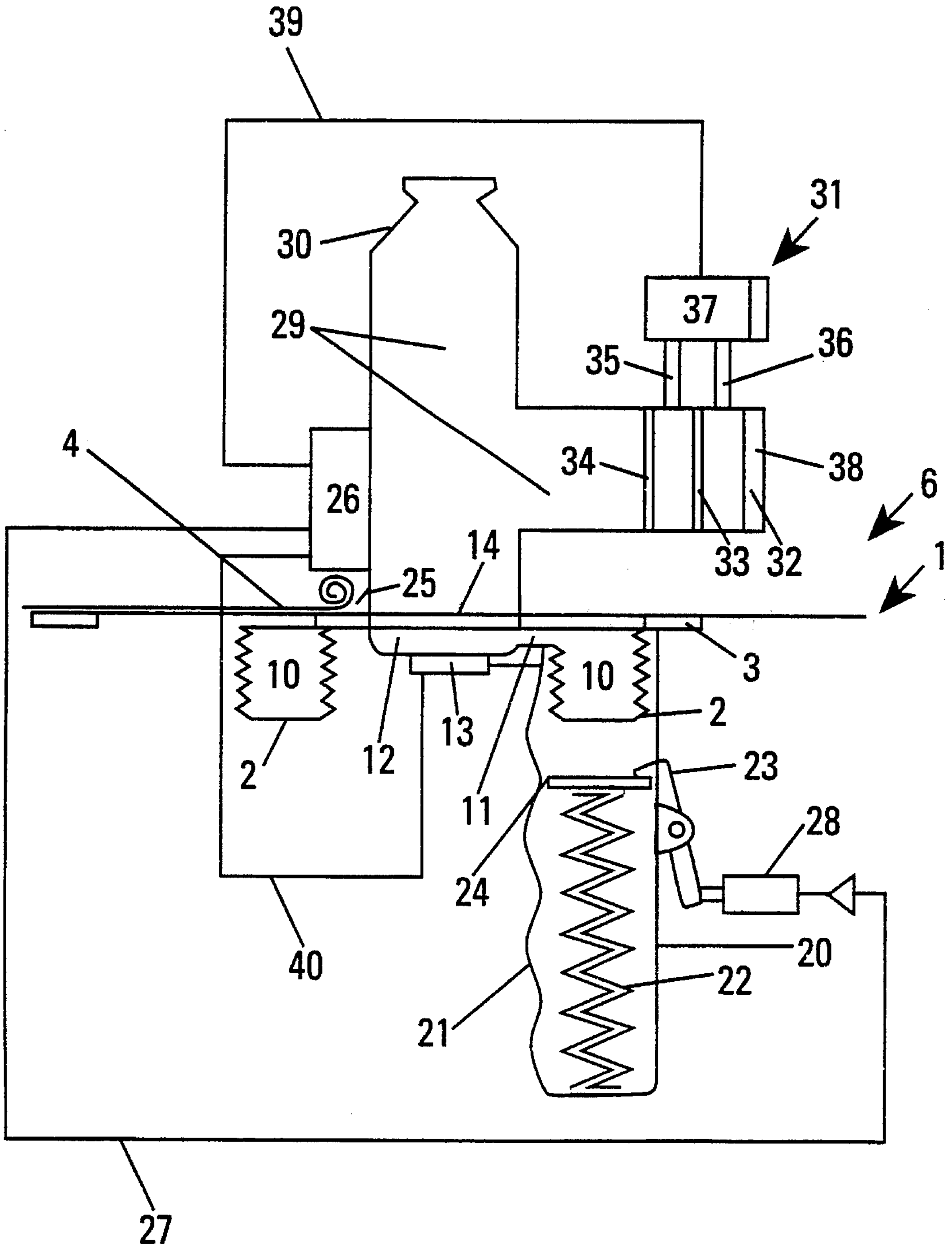
FIG. 9 is a cross-sectional plan view of a disposable package of the invention positioned above a piston of a dispensing device.

The device 6 shown in FIG. 9 is loaded with a disposable package 1, which package is not included within a cassette. The package 1 is comprised of a plurality of containers 2. Each container 2 includes a drug formulation 10 and is in fluid connection via a channel 11 with the resonance cavity 12. The cavity 12 is covered by the porous membrane 14. Further, a vibrating mechanism 13 of the device 6 is positioned such that it is located directly below the resonance cavity 12 when that resonance cavity is in the drug delivery position.

The device 6 is a hand-held, portable device which is comprised of (a) a device for holding a disposable package with at least one but preferably a number of drug containers, (b) a mechanical mechanism for forcing the contents of a container (on the package) from a porous membrane on the container and preferably (c) a monitor for analyzing the inspiratory flow of a patient and (d) a switch for automatically releasing or firing the mechanical means after the inspiratory flow and/or volume reaches a threshold level. The device for holding the disposable package may be nothing more than a narrow opening created between two outwardly extending bars or may include additional components such as one or more wheels, sprockets or rollers rotably mounted on the end(s) of such bars. The rollers may be spring mounted so as to provide constant pressure against the surface(s) of the package. The device may also include a transport mechanism which may include providing drive power to the roller(s) so that when they are rotated, they move the package from one container to the next. The power driving the roller(s) is programmed to rotate the rollers only enough to move the package from one container to the next. In order to use the device, the device must be "loaded," i.e. connected to a package (or cassette holding a package) which includes drug dosage units having liquid, flowable formulations of pharmaceutically active drug therein. The entire device is selfcontained, light weight (less than 1 kg preferably less than 0.5 kg loaded) and portable.

The device may include a mouth piece at the end of the flow path, and the patient inhales from the mouth piece which causes an inspiratory flow to be measured within the flow path which path may be in a non-linear flow-pressure relationship. This inspiratory flow causes an air flow transducer to generate a signal. This signal is conveyed to a microprocessor which is able to convert, continuously, the signal from the transducer in the inspiratory flow path to a flow rate in liters per minute. The microprocessor can further integrate this continuous air flow rate signal into a representation of cumulative inspiratory volume. At an appropriate point in the inspiratory cycle, the microprocessor can send a signal to an actuation means and the vibration device below the resonance cavity. When the actuation means is signaled, it causes the mechanical means to force drug from a container on the cellular array into the inspiratory flow path of the device and ultimately into the patient's lungs. After being released, the drug and propellant will pass through a porous membrane which is vibrated to aerosolize the formulation and thereafter the lungs of the patient.

It is important to note that the firing threshold of the device is preferably not based on a single criterion such as the rate of air flow through the device or a specific time after the patient begins inhalation. The firing threshold is based on an analysis of the patient's inspiratory flow profile. This means that the microprocessor controlling the device takes into consideration the instantaneous air flow rate as well as the cumulative inspiratory flow volume when it determines the optimal point in the patient's inspiratory cycle which would be most preferable in terms of reproducibly delivering the same amount of drug to the patient with each release of drug.

The device preferably includes a means for recording a characterization of the inspiratory flow profile for the patient which is possible by including a microprocessor in combination with a read/write memory means and a flow measurement transducer. By using such devices, it is possible to change the firing threshold at any time in response to an analysis of the patient's inspiratory flow profile, and it is also possible to record drug dosing events over time. In a particularly preferred embodiment the characterization of the inspiratory flow can be recorded onto a recording means on the cellular array.

FIG. 9 shows a cross-sectional view of a hand held, self-contained, portable, breath-actuated inhaler device 6 of the present invention. The device 6 is shown with a holder 20 having cylindrical side walls and a hand grip 21. The holder 20 is "loaded" in that it includes a package 1. The package 1 includes a plurality of containers 2.

The embodiment shown in FIG. 9 is a simple version of the invention and is not the preferred embodiment. The device 6 may be manually actuated and loaded. More specifically, the spring 22 may be compressed by the user until it is forced down below the actuation mechanism 23. When the user pushes the actuation mechanism 23 the spring 22 is released and the mechanical means in the form of a plate 24 is forced upward against a container 2. When the container 2 is compressed its contents are forced out through the channel 11 and membrane 14 and aerosolized. Another container 2 shown to the left is unused. A top cover sheet 4 has been peeled away from the top of the membrane 14 by a peeling means 25. The embodiment of FIG. 9 could provide the same results as a conventional metered dose inhaler. However, the device of FIG. 9 would not require the use of low boiling point propellants such as low boiling point fluorocarbons. Numerous additional features and advantages of the present invention can be obtained by utilizing the monitoring and electronic components described below.

It is important to note that a variety of devices can be used in order to carry out the methodology (including the respiratory disease treatment methodology) of the present invention. However, the device must be capable of aerosolizing drug formulation in a container and preferably does such based on pre-programmed criteria which are readable by the microprocessor 26. The details of the microprocessor 26 and the details of other drug delivery devices which include a microprocessor and pressure transducer of the type used in connection with the present invention are described and disclosed within U.S. Pat. No. 5,404,871 issued Apr. 11, 1995 entitled "Delivery of Aerosol Medications for Inspiration" which application is incorporated in its entirety herein by reference, and it is specifically incorporated in order to describe and disclose the microprocessor and program technology used therewith. The use of such a microprocessor with a drug delivery device is disclosed in our earlier filed U.S. application Ser. No. 08/065,660 filed May 21, 1993 incorporated herein by reference. The pre-programmed information is contained within a nonvolatile memory which can be modified via an external device. In another embodiment, this pre-programmed information is contained within a "read only" memory which can be unplugged from the device and replaced with another memory unit containing different programming information. In yet another embodiment, microprocessor 26, containing read only memory which in turn contains the pre-programmed information, is plugged into the device. For each of these three embodiments, changing the programming of the memory device readable by microprocessor 26 will radically change the behavior of the device by causing microprocessor 26 to be programmed in a different manner. This is done to accommodate different drugs for different types of treatment.

Microprocessor 26 sends signals via electrical connection 27 to electrical actuation device 28 which actuates the means 23 which fires the mechanical plate 24 forcing drug formulation in a container 2 to be aerosolized so that an amount of aerosolized drug is delivered into the inspiratory flow path 29. The device 28 can be a solenoid, motor, or any device for converting electrical to mechanical energy. Further, microprocessor 26 keeps a record of all drug dosing times and amounts using a read/write non-volatile memory which is in turn readable by an external device. Alternatively, the device records the information onto an electronic or magnetic strip on the tape 3 of the package 1. The recorded information can be read later by the care-giver to determine the effectiveness of the treatment. In order to allow for ease of use, it is possible to surround the inspiratory flow path 29 with a mouth piece 30 which can be specifically designed to fit the mouth of a particular patient using the device.

The electrical actuation means 28 is in electrical connection with the flow sensor 31 which is capable of measuring a flow rate of about 0 to about 800 liters per minute. It should be noted that inhalation flow rates are less than exhalation rates, e.g. max for inhalation 200 lpm and 800 lpm for exhalation. The flow sensor 31 includes screens 32, 33 and 34 which are positioned approximately ¾ apart from each other. Tubes 35 and 36 open to the area between the screens 32, 33 and 34 with the tubes 35 and 36 being connected to a conventional differential pressure transducer 37. Another transducer designed to measure outflow through the opening 38 is also preferably included or the flow sensor 31 is designed so that the same components can measure inflow and outflow. When the user draws air through inspiratory flow path 29, air is passed through the screens 32, 33 and 34 and the air flow can be measured by the differential air pressure transducer 37. Alternatively, other means to measure pressure differential related to air flow, such as a conventional measuring device in the air way, may be used. The flow sensor 31 is in connection with the electrical actuation means 28 (via the connector 39 to the processor 26), and when a threshold value of air flow is reached (as determined by the processor 26), the electrical actuation means 28 fires the release of a mechanical means 23 releasing the plate 24 which forces the release of formulation from a container 2 so that a controlled amount of respiratory drug is delivered to the patient. The microprocessor 26 is also connected via connector 40 to the vibrating device 13 which is activated when fluid 10 enters the vibrator cavity 12.

The vibrator 13 is designed so as to generate vibrations which affect the particle formation of formulation being forced out of the pores within the membrane 14. The frequency of the vibrations can be varied depending upon the size of the pores in the membrane 14 and the viscosity of the formulation 10 and pressure present within the container 2. However, in general, the vibrations are within the range of about 800 kilohertz to about 4,000 kilohertz.

The device of FIG. 9 does not show the cassette 5 of FIG. 2, but does show all of the components present within the single, hand-held, portable breath actuated device, e.g. the microprocessor 26 and flow sensor 31 used to provide the electronic breath actuated release of drug. The device of FIG. 9 includes a holding means and mechanical means and preferably operates electronically, i.e. the actuation means is preferably not directly released by the user. The patient inhales through inspiratory flow path 29 which can form a mouth piece 30. Air enters the device via the opening 38. The inhaling is carried out in order to obtain a metering event using the differential pressure transducer 37. Further, when the inspiratory flow meets a threshold of a pre-programmed criteria, the microprocessor 26 sends a signal to an actuator release electrical mechanism 28 which actuates the mechanical means 23, thereby releasing a spring 22 and plate 24 or equivalent thereof, forcing aerosolized formulation into the channel 11, cavity 12 (vibrated by the vibrator 13) and out of the membrane 14 into the flow path 29. Further details regarding microprocessors 26 of FIG. 9 are described within co-pending U.S. patent application entitled "An Automatic Aerosol Medication Delivery System and Methods", issued as U.S. Pat. No. 5,394,866 on Mar. 7, 1995, which application is incorporated herein by reference in its entirety and specifically incorporated in order to describe and disclose flow measurements, the microprocessor and program technology used therewith.

Microprocessor 26 of FIG. 9 includes an external non-volatile read/write memory subsystem, peripheral devices to support this memory system, reset circuit, a clock oscillator, a data acquisition subsystem and a visual annunciator subsystem. The discrete components are conventional parts which have input and output pins configured in a conventional manner with the connections being made in accordance with instructions provided by the device manufacturers. The microprocessor used in connection with the device of the invention is designed and programmed specifically so as to provide controlled and repeatable amounts of respiratory drug to a patient upon actuation. The microprocessor must have sufficient capacity to make calculations in real time. Adjustments can be made in the program so that when the patient's inspiratory flow profile is changed such is taken into consideration. This can be done by allowing the patient to inhale through the device as a test (monitoring event) in order to measure air flow with preferred drug delivery points determined based on the results of several inhalations by each particular patient. This process can be readily repeated when the inspiratory flow profile is changed for whatever reason. When the patient's lung function has decreased the program will automatically back down in terms of the threshold levels required for release of drug. This "back down" function insures drug delivery to a patient in need but with impaired lung function. Determination of optimal drug delivery points in the inspiratory flow can be done at each dosing event, daily, weekly, or with the replacement of a new cellular array in the device.

The microprocessor 26 of the present invention, along with its associated peripheral devices, can be programmed so as to prevent triggering the actuation mechanism 28 more than a given number of times within a given period of time. This feature makes it possible to prevent overdosing the patient. The overdose prevention feature can be particularly designed with each individual patient in mind or designed with particular groups of patients in mind. For example, the microprocessor can be programmed so as to prevent the release of more than approximately 200 μg of a given respiratory drug per day when the patient is normally dosed with approximately 100 μg of drug per day. The device can be designed to switch off this lock-out function so that drug can be delivered in an emergency situation.

The systems can also be designed so that only a given amount of a particular drug such as a respiratory drug is provided at a given dosing event. For example, the system can be designed so that only approximately 10 μg of respiratory drug is given in a given 15-minute period over which the patient will make approximately 10 inhalations with 1 μg of drug being delivered with each inhalation. By providing this feature, greater assurances are obtained with respect to delivering the respiratory drug gradually over time and thereby providing relief from the symptoms of respiratory disease without overdosing the patient.

The microprocessor of the invention can be connected to external devices permitting external information to be transferred into the microprocessor of the invention and stored within the non-volatile read/write memory available to the microprocessor. The microprocessor of the invention can then change its drug delivery behavior based on this information transferred from external devices. All of the features of the invention are provided in a portable, programmable, battery-powered, hand-held device for patient use which has a size which compares favorably with existing metered dose inhaler devices.

The microprocessor of the present invention is programmed so as to allow for monitoring and recording data from the inspiratory flow monitor without delivering drug. This is done in order to characterize the patient's inspiratory flow profile in a given number of monitoring events, which monitoring events preferably occur prior to dosing events. After carrying out a monitoring event, the preferred point within the inspiratory cycle for drug delivery can be calculated. This calculated point is a function of measured inspiratory flow rate as well as calculated cumulative inspiratory flow volume. This information is stored and used to allow activation of the electronic actuation means when the inhalation cycle is repeated during the dosing event.

Creating Aerosols

In order for any aspects of the present invention to be utilized an aerosol must be created. When formulation is initially forced through the pores of the porous membrane the formulation exits as streams. However, the streams are unstable and will, do to factors such as surface tension, break up into droplets on their own. The size of the droplets will be affected by factors such as the pore size, temperature, and the surface tension of the formulation forced through the pores. In general, if there is no vibration, the size of the particles within the dispersion will vary over a range and will include a large number of particles which are too large to be readily inhaled. Accordingly, not all the drug can effectively enter the lungs for intrapulmonary delivery to have the desired effects. To create an aerosol with a desired size dispersion of particles, the streams of liquid must be broken into particles having a diameter which is sufficiently small such that the patient can inhale the particles into the pulmonary tree. Although the particle size will vary depending on factors such as the particular type of formulation being aerosolized, in general, the preferred particle size is in the range of about 0.5 micron to about 12 microns. In order to obtain small particle sizes sufficient to aerosolize a formulation a number of different porous membranes and vibrating devices can be utilized and the present invention is intended to encompass such aerosolizing systems.

The pharmaceutical formulations in the containers are forced through the tiny openings (pores) in the polycarbonate or polyester membrane while the liquid, container and/or openings are simultaneously subjected to vibration. By vibrating at a particular frequency it is possible to form extremely small particles and create a fine mist aerosol. The particle size is determined by the size of the openings on the porous structure through which the liquid formulation is forced, the rate at which the fluid is forced from the container, and vibration frequency. More specifically, the aerosol particle size is a function of the diameter of the openings or pores through which the formulation is forced, vibration frequency, viscosity, liquid surface tension, and pressure at which liquid is extruded through the membrane. In essence, the particle size diameter will be approximately twice the pore size diameter with a margin of error of approximately ±20% or less. For example, if the membrane used to cover the drug dosage unit includes pores having a diameter of 2 microns the aerosolized particles formed will have a size of approximately 3.6 to 4.4 microns in diameter. This relationship between particle size and pore diameter appears to hold over a pore sized diameter of approximately 0.5 micron to about 50 microns. Accordingly, it is possible to use membranes with pores therein having pore sizes of sufficient diameter to form aerosols having a particle sized diameter of about one micron to about 100 microns—although preferred particles have a diameter of about 0.5 to 12 microns. Different types of membrane materials can be used in connection with the invention. In general, the membrane will have a density of about 0.25 to about 3.0 $mg/cm^2$, more preferably about 1.7 $mg/cm^2$ and a thickness in the range of from about 2 to about 20 μm, more preferably about 14 to 16 μm. The membrane will cover the entire opening of the container. The size and the shape of the opening can vary and will generally have an area in the range of about 0.025 $cm^2$ to about 1.0 $cm^2$ but more preferably about 0.1–0.2 $cm^2$.

The various components of the invention are generally used to create a "monodisperse" aerosol wherein all the particles within the aerosol created have essentially the same particle size. By adjusting parameters such as the surface tension of the formulation, pore hole size, and the air flow speed the size of the monodispersed particles can be adjusted within a very narrow range of size e.g. the particles will have a size diameter equal to each other with a margin of error of approximately ±10% or less, more preferably ±5% or less.

Figure 11:
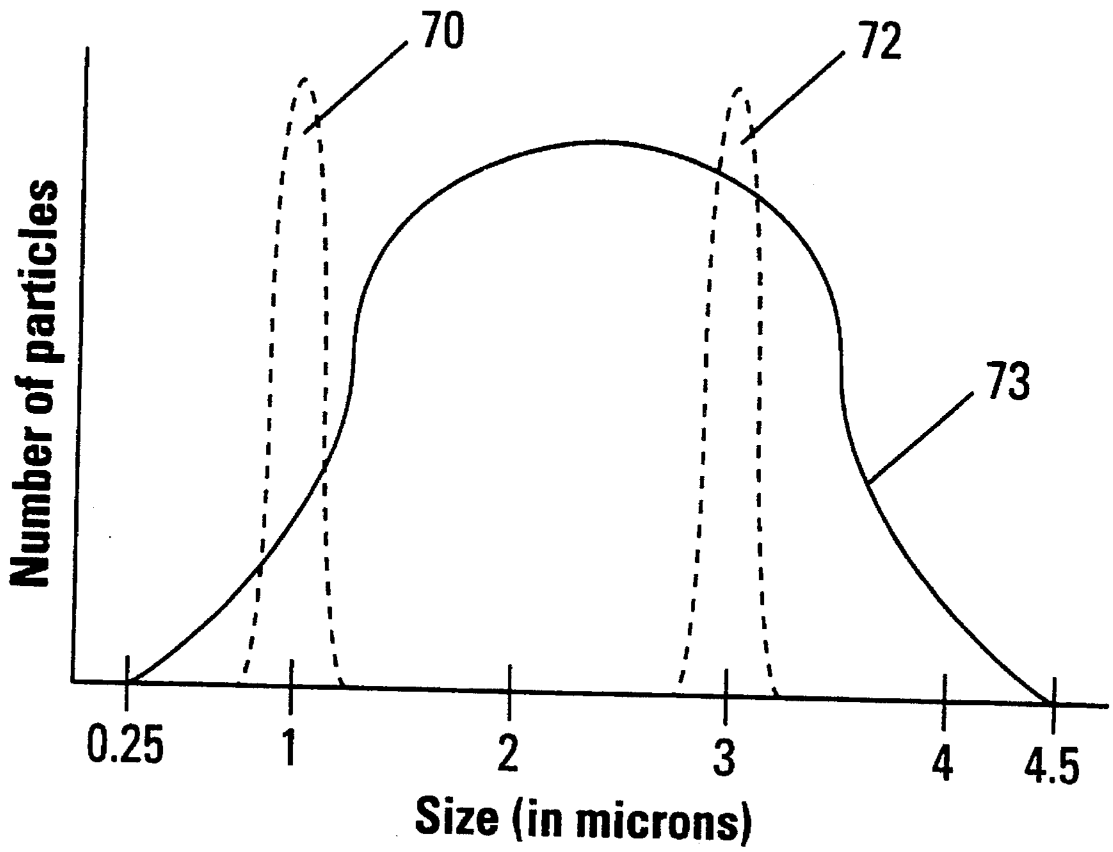
FIG. 11 is a graph of particle size versus number of particles in three aerosol dispersions.

FIG. 11 shows a graph of particle size versus the number of particles. The first peak 70 shows that nearly all the particles are approximately 1 micron in diameter, where as the peak 72 shows nearly all of the particles have a diameter of approximately 3 microns. The curve 73 shows a more even distribution of particles from about 0.25 micron to about 4.5 microns. Nebulizer devices may be capable of creating particle dispersion curves such as the curve 73. The present invention can vary the frequency of the vibrating device in order to create a particle size distribution as per the curve 73. This is done by changing the frequency during a single breath while formulation is forced through the membrane 14. Alternatively, the frequency can be set to create all the particles within a very narrow distribution as shown within the curves 70 and 72. Depending upon the type of disease being treated, the vibration frequency can be set and the desired results obtained.

Multi-disperse aerosol

As indicated above, the formulation is forced through the pores of the porous membrane to create streams. Along with the stream of formulation exiting the pores an air flow is created out of air dispersion vents. The speed of the air flow and its volume can be adjusted in any desired manner so as to allow for the collision of some but not all of the particles thereby causing an aggregation of the colliding particles to create particles of different sizes.

In accordance with another method the vibration frequency can be varied. This vibration frequency can be gradually varied over the time which formulation is dispersed or can be oscillated between a high and a low point thereby varying the point at which the streams exiting the pores are cut to create different size particles.

Lastly, the particle size can be varied by using a membrane which has a range of different pore sizes. All or any of these three techniques can be used in combination with each other to obtain the desired particle size dispersion within the aerosol. In addition to using these features independently or together it is possible to vary other parameters such as the viscosity and surface tension of the formulation.

Dry, disposable, porous membranes

The porous membranes of the invention are used only once. Accordingly, clogging of the pores is avoided or substantially reduced as compared to situations where a nozzle is used repeatedly. The membrane is preferably dry prior to use. Further, a porous membrane or aerosol creating the system of the type described herein provides relatively small particle sizes within a narrow particle size distribution. Accordingly, the smallest particles produced will not vary greatly in size as compared to the largest particles produced. More specifically, two-thirds or more of the particles produced will, preferably, have a particle size within 20% of the mean particle size. In that the preferred mean particle size is about 5 microns, the system will produce an aerosol wherein two-thirds or more of the particles within the aerosol have a particle size in the range of about 4 microns to about 6 microns. The system can aerosolize from about 50 μl to about 300 μl, more preferably, 200 μl of liquid from a single container. The contents of a container is generally aerosolized in a relatively short period of time, e.g., 1 second or less and inhaled by the patient in a single breath.

The porous membranes used on the packages of the present invention can be produced wherein the openings or pores are all uniform in size and are positioned at uniform distances from each other. However, the openings can be varied in size and randomly placed on the membrane. If the size of the openings is varied the size of the particles formed will also vary. In general, it is preferable to maintain uniform opening sizes in order to create uniform particle sizes and it is particularly preferable to have the opening sizes within the range of about 0.25 to about 6 microns which will create particle sizes of about 0.5 to 12 microns which are preferred with respect to inhalation applications. When the openings have a pore size in the range of 0.5 to 3 microns they will produce an aerosol having particle sizes in the range of 1 to 6 microns which is particularly useful for treating the bronchioles and alveoli. Pore sizes having a diameter of about 3 to 5 microns will produce particle sizes having a diameter of about 6 to 10 microns which are particularly useful with respect to treating the bronchi.

In accordance with the present invention the porous membrane preferably includes pore sizes in the range of 0.5 micron to about 50 microns. Further, the pores are preferably separated, one from the other, in a random pattern providing about $1\times10^4$ to about $1\times10^8$ pores/$cm^2$. Further, the pore diameter indicates that at least 75% of the pores on the membrane fall within the prescribed range and preferably indicates that 85% or more of the pores fit within the prescribed range. Uniformity in pore size is desirable for creating uniformity in the particle size of the aerosol being delivered which is important with respect to maintaining consistency in dosing.

A variety of different types of materials can be used for forming the pore openings of the drug dosage units. It is important that the membrane material which the pores are placed in has sufficient structural integrity such that when the liquid in the container is forced against the material the material will not rupture and the pore size will remain essentially constant under pressure. It has been found that porous ceramic oxides may be used as well as porous glasses, and metal frets, compressed porous plastics, and certain membranes including polycarbonate membranes including one preferred membrane referred to as "Nuclepore®" polycarbonate membranes produced by Costar Corporation and "Isopore®" by Millipore Corporation which are commercially produced for use as filters to have a pore diameter in the range of 0.015 to 12 microns.

Although the thickness of the membrane material may be of any thickness, it is desirable for the material to be particularly thin e.g. less than one millimeter and more preferably less than 20 μ with particularly preferred components having a thickness in the range of about 10 μ to 15 μ. As the thickness of this material is increased the amount of energy necessary to force the liquid through the membrane material is increased. Since the device of the present invention is a hand-held device it is important to produce materials which require the use of small amounts of energy in order to create the aerosol in that the energy supply is somewhat limited.

In order to reduce the amount of energy needed to force the formulation through the pores of the porous membrane it is possible to produce the pores in different configurations. Although the pores are generally cylindrical in shape they can be non-cylindrical (e.g. hourglass shaped) and are preferably conically shaped. The conically shaped pores have the wide end of the cone shape facing towards the resonance cavity where the drug formulation is dispersed from and the small end of the cone at the outer edge of the membrane from which the particles are dispersed from. The small end of the conically shaped pores has a diameter in the range of 0.25 to 6 microns. The surface of the conically shaped pores may have a coating thereon of a reduced friction type of material such as Teflon®-type materials.

Vibration device

In most instances, a preferred aerosol dispersion will not be created merely by forcing a liquid through a porous membrane of the type described above. The porous membrane must be vibrated ultrasonically in order to produce an aerosol having the desired particle size. Such vibrations can be carried out by connecting an ultrasonic vibrator to the drug delivery device. The vibrator may be positioned on different components of the drug delivery device but is preferably positioned directly beneath the resonance cavity and close to the porous membrane.

The ultrasonic vibrations are preferably at right angles to the plane of the membrane and can be obtained by the use of a piezoelectric ceramic crystal or other suitable vibration device. The piezoelectric crystal is connected to a piston or the porous membrane by means of an attenuator horn or acoustic conduction mechanism, which when correctly matched with the piezoelectric crystal frequency, efficiently transmits ultrasonic oscillations of the piezoelectric crystal to the resonance cavity and the porous polycarbonate membrane and if sized correctly permits the ultrasonic energy to be focused in the polycarbonate membrane allowing for maximum use of the energy towards aerosolizing the liquid formulation. The size and shape of the attenuator horn is not of particular importance. It is preferred to maintain a relatively small size in that the device is hand held. The components are chosen based on the particular material used as the porous material, the particular formulation used and with consideration of the velocity of ultrasonic waves through the membrane to achieve a harmonic relationship at the frequency being used.

A high frequency signal generator drives the piezoelectric crystal. This generator is capable of producing a signal having a frequency of from about 800 kilohertz (Khz) to about 4,000 kilohertz. The power output required depends upon the amount of liquid being nebulized per unit of time and the area and porosity of the polycarbonate membrane used for producing the drug dosage unit and/or the efficiency of the connection.

The vibration is applied while the liquid is being forced from the pores of the polycarbonate membrane. The pressure required for forcing the liquid out can be varied depending on the liquid, the size of the pores and the shape of the pores but is generally in the range of about one to 200 psi, preferably 25 to 125 psi and may be achieved by using a piston, roller, bellows, a blast of forced compressed gas, or other suitable device. The vibration frequency used and the pressure applied can be varied depending on the viscosity of the liquid being forced out and the diameter and length of the openings or pores. In general, the present invention does not create effective aerosols if the viscosity of the liquid is greater than about 50 centipoises.

When small aerosolized particles are forced into the air, the particles encounter substantial frictional resistance. This causes the particles to slow down quickly and may result in particles colliding into each other and combining, which is undesirable with respect to maintaining the preferred particle size distribution within the aerosol. In order to aid in avoiding the particle collision problem, it is preferable to include one or more openings in the cassette or package in close proximity to the porous membrane. Air or any other gas is forced through these openings as the aerosol is forced from the container. Accordingly, an air flow is created toward the patient and away from the nozzle opening which carries the formed particles along and aids in preventing their collision with each other. The amount of gas forced from the openings will vary depending upon the amount of aerosol being formed. However, the amount of gas is generally five to two hundred times the volume of the liquid formulation within the container. Further, the flow velocity of the gas is generally about equal to the flow velocity of the aerosolized particles being forced from the nozzle. The shape of the container opening, the shape of the membrane covering that opening, as well as the positioning and angling of the gas flow and particle flow can be designed to aid in preventing particle collision. When the two flow paths are substantially parallel, it is desirable to shape the opening and matching membrane so as to minimize the distance between any edge of the opening and the center of the opening. Accordingly, it is not desirable to form a circular opening which would maximize the distance between the outer edges of the circle and the center of the circle, whereas it is desirable to form an elongated narrow rectangle. Using such a configuration makes it possible to better utilize the air flow relative to all of the particles being forced from the container. When a circular opening is used, particles which are towards the center of the circle may not be carried along by the air being forced from the openings and will collide with each other. The elongated rectangle could be formed in a circle, thereby providing an annular opening and air could be forced outward from the outer and inner edges of the circle formed.

Method of Administration

The method and device of the invention provides a number of features which make it possible to achieve the controlled and repeatable dosing procedure required for the treatment of diseases, particularly respiratory diseases such as asthma.

The method of the invention involves the release of a liquid, flowable drug from individual containers which may be interconnected in a package held in a cassette. This is desirable in that the liquid, flowable drug is packaged under a sterile environment and therefore does not require and preferably does not include additional materials such as antifungal, bacteriostatics, and preservatives which would normally be required in a liquid formulation if the formulation was to be opened, exposed to air, closed and later used again. The present invention does not require the use of low boiling point propellants such as low boiling point fluorocarbons. The use of such low boiling point propellants in conventional metered dose inhaler devices is desirable because such propellants eliminate the need for preservatives, antifungal and bacteriostatic compounds. However, there are potential environmental risks to using low boiling point fluorocarbons. Accordingly, the present invention provides potential environmental benefits and would be particularly useful if government regulations prevented further use of devices which dispensed low boiling point fluorocarbons.

In addition to environmental advantages, the present invention offers advantages due to the relatively slow speed at which the aerosol dispersion is delivered to the patient. A conventional metered dose inhaler device discharges the aerosol outward at a relatively high rate of speed which causes a large amount of the aerosol particles to make contact with the inside of the patient's mouth and the back of the patient's throat. This decreases the amount of drug actually administered to the patient's lungs as compared with the present system, wherein the aerosol is delivered at a relatively slow rate of speed and can be inhaled slowly by the patient.

The method preferably uses a drug delivery device which is not directly actuated by the patient in the sense that no button is pushed nor valve released by the patient applying physical pressure. On the contrary, the device of the invention provides that the actuation mechanism which causes drug to be forced from a container is fired automatically upon receipt of a signal from a microprocessor programmed to send a signal based upon data received from a monitoring device such as an airflow rate monitoring device. A patient using the device withdraws air from a mouthpiece and the inspiratory rate, and calculated inspiratory volume of the patient is measured one or more times in a monitoring event which determines an optimal point in an inhalation cycle for the release of a dose of any desired drug. Inspiratory flow is preferably measured and recorded in one or more monitoring events for a given patient in order to develop an inspiratory flow profile for the patient. Recorded information is preferably analyzed by the microprocessor in order to deduce a preferred point within the patient's inspiratory cycle for the release of drug with the preferred point being calculated based on the most likely point to result in a reproducible delivery event.

A flow rate monitoring device continually sends information to the microprocessor, and when the microprocessor determines that the optimal point in the respiratory cycle is reached, the microprocessor actuates a component which fires a mechanical means (and activates the vibration device) which causes drug to be forced out of the container and aerosolized. Accordingly, drug is always delivered at a pre-programmed place in the inspiratory flow profile of the particular patient which is selected specifically to maximize reproducibility of drug delivery and peripheral deposition of the drug. It is pointed out that the device of the present invention can be used to, and actually does, improve the efficiency of drug delivery. However, this is not the most important feature. A more important feature is the reproducibility of the release of a tightly controlled amount of drug (with a narrow range of particle size) at a particular point in the respiratory cycle so as to assure the delivery of a controlled and repeatable amount of drug to the lungs of each individual patient. Further, this is accomplished without the use of fluorocarbons and/or bacteriostatic compounds.

The combination of automatic control of the drug release mechanism, combined with frequent monitoring events in order to calculate the optimal flow rate and time for the release of respiratory drug, combine to provide a repeatable means of delivering respiratory drug to a patient. Because the drug release mechanism is fired automatically and not manually, it can be predictably and repeatedly fired at that same point in the inspiratory cycle. Because dosing events are preferably preceded by monitoring events, the point in the inspiratory cycle of the release can be readjusted based on the particular condition of the patient. For example, patients suffering from asthma have a certain degree of pulmonary insufficiency which may well change with the administration of drug. These changes will be taken into account in the monitoring event by the microprocessor which will readjust the point of release of the respiratory drug in a manner calculated to provide for the administration of an amount of respiratory drug to the patient presently needed by the patient at each dosing event.

When administering drug using the inhalation device of the present invention, the entire dosing event can involve the administration of anywhere from 10 μg to 1,000 mg of drug formulation, but more preferably involves the administration of approximately 50 μg to 10,000 μg of drug formulation. This amount of drug is in a liquid form or is dissolved or dispersed within a pharmaceutically acceptable, liquid, excipient material to provide a liquid, flowable formulation which can be readily aerosolized. The container will include the formulation having drug therein in an amount of about 50 μl to 300 μl, more preferably about 200 μl. The large variation in the amounts which might be delivered are due to different drug potencies and different delivery efficiencies for different devices. The entire dosing event may involve several inhalations by the patient with each of the inhalations being provided with drug from the device. For example, the device can be programmed so as to release the contents of a single container or to move from one container to the next on a package of interconnected containers. Delivering smaller amounts from several containers can have advantages. Since only small amounts are delivered from each container and with each inhalation, even a complete failure to deliver drug with a given inhalation is not of great significance and will not seriously disturb the reproducibility of the dosing event. Further, since relatively small amounts are delivered with each inhalation, the patient can safely administer a few additional micrograms of drug (or milligrams for some drugs) without fear of overdosing.

In addition to drug potency and delivery efficiency, drug sensitivity must be taken into consideration. The present invention makes it possible to vary dosing over time if sensitivity changes and/or if user compliance and/or lung efficiency changes over time.

Based on the above, it will be understood that the dosing or amount of drug (and in particular respiratory drug) actually released from the device can be changed based on the most immediately prior monitoring event wherein the inspiratory flow of a patient's inhalation is measured.

Variations in doses are calculated by monitoring the effect of one or more lung function parameters in response to known amounts of respiratory drug released from each container and delivered to the patient. If the response in changing measured lung function parameters is greater than with previous readings, then the dosage (number of containers released) is decreased or the minimum dosing interval is increased. If the response in changing measured lung function parameters is less than with previous readings, then the dosing amount is increased or the minimum dosing interval is decreased. The increases and decreases are gradual and are preferably based on averages (of 10 or more readings of lung function parameter after 10 or more dosing events) and not a single dosing event and monitoring event. The preferred drug delivery device of the present invention can record dosing events and lung function parameters over time, calculate averages and deduce preferred changes in administration of respiratory drug.

One of the important features and advantages of the present invention is that the microprocessor can be programmed to take two different criteria into consideration with respect to dosing times. Specifically, the microprocessor can be programmed so as to include a minimum time interval between doses i.e. after a given delivery another dose cannot be delivered until a given period of time has passed. Secondly, the timing of the device can be programmed so that it is not possible to exceed the administration of a set maximum amount of drug within a given time. For example, the device could be programmed to prevent dispersing more than 200 μg (or two 100 μg containers of drug) of a particular drug within one hour. More importantly, the device can be programmed to take both criteria into consideration. Thus, the device can be programmed to include a minimum time interval between doses and a maximum amount of drug to be released within a given time period. For example, the microprocessor could be programmed to allow the release of a maximum of 200 μg of a given drug during an hour which could only be released in amounts of 25 μg with each release being separated by a minimum of five minutes.

The dosing program can be designed with some flexibility. For example, if the patient normally requires 250 μg per day of respiratory drug, the microprocessor of the inhalation device can be programmed to provide a warning after 250 μg have been administered within a given day and to continue the warning thereafter to alert the user of possible overdoses. By providing a warning and not a lock-out, the device allows for the patient to administer additional respiratory drug, if needed, due to a decreased lung function and/or account for misdelivery of respiratory drug such as due to coughing or sneezing during an attempted delivery.

The ability to prevent overdosing is a characteristic of the device due to the ability of the device to monitor the amount of respiratory drug released and calculate the approximate amount of respiratory drug delivered to the patient based on monitoring a variety of lung function parameters. The ability of the present device to prevent overdosing is not merely a monitoring system which prevents further manual actuation of a button. As indicated above, the device used in connection with the present invention is not manually actuated, but is fired in response to an electrical signal received from a microprocessor (which received data from a monitoring device such as a device which monitors inspiratory flow) and allows the actuation of the device upon achieving an optimal point in a inspiratory cycle. When using the present invention, each actuation of the device will administer drug to the patient in that the device is fired in response to patient inhalation. More specifically, the preferred embodiment of the device does not allow for the release of respiratory drug merely by the manual actuation of a button to fire a burst of respiratory drug into the air or a container. A variety of different embodiments of the dispersion device of the invention are contemplated. In accordance with one embodiment it is necessary to carry out manual cocking of the device. This means that energy is stored such as by retracting a spring so that, for example, a piston can be positioned below the drug containing container. In a similar manner a piston connected to a spring can be withdrawn so that when it is released it will force air through the air dispersion vents. Automatic cocking of forced storing systems for both the drug formulation and the air flow may be separate or in one unit. Further, one may be manual whereas the other may be done automatically. In accordance with one embodiment the device is cocked manually but fired automatically and electronically based on monitoring the patients inspiratory flow.

The microprocessor of the present invention preferably includes a timing device. The timing device can be electrically connected with visual display signals as well as audio alarm signals. Using the timing device, the microprocessor can be programmed so as to allow for a visual or audio signal to be sent when the patient would be normally expected to administer respiratory drug. In addition to indicating the time of administration (preferably by audio signal), the device can indicate the amount of respiratory drug which should be administered by providing a visual display. For example, the audio alarm could sound alerting the patient that respiratory drug should be administered. At the same time, the visual display could indicate "one dosage unit" as the amount of drug (number of containers) to be administered. At this point, a monitoring event could take place. After completion of the monitoring event, administration would proceed and the visual display would continually indicate the remaining amount of respiratory drug which should be administered. After the predetermined dose (indicated number of containers) had been administered, the visual display would indicate that the dosing event had ended. If the patient did not complete the dosing event by administering the stated amount of drug, the patient would be reminded of such by the initiation of another audio signal, followed by a visual display instructing the patient to continue administration.

Additional information regarding dosing with drugs can be found within Harrison's—Principles of Internal Medicine (most recent edition) and the Drug Evaluation Manual, 1993 (AMA-Division of Drugs and Toxicology), both of which are published by McGraw Hill Book Company, New York, incorporated herein by reference to disclose conventional information regarding dosing of drugs and in particular respiratory drugs as well as other useful drugs and formulations.

Supplemental Treatment Methodology

The present invention can be used to deliver many types of drugs. Specifically, the disposable packages, cassettes and drug delivery devices can be used to deliver drugs which have a systemic effect (e.g. narcotics, proteins such as DNAse and antibiotics) as well as drugs which have a local effect primarily on the lungs (e.g. bronchodilators). Because the present invention allows drug delivery directly to the lungs there are certain advantages with respect to using the invention for the delivery of drugs to treat respiratory diseases. For this reason, much of the operation of the invention is described in connection with the delivery of respiratory drugs. However, the invention is not limited to respiratory drugs and the examples described herein would apply with respect to the delivery of drugs having a systemic effect. This is true also with respect to the supplemental treatment methodology described below even though this methodology is described with specific reference to respiratory diseases being treated with respiratory drugs.

Patients suffering from a given disease such as a respiratory disease may be treated solely with respiratory drug as indicated above, i.e. by intrapulmonary delivery. However, it is possible to treat such patients with a combination of intrapulmonary delivery and other means of administration such as oral administration. The oral drug is preferably given in amount so as to maintain a baseline level of drug within the circulatory system which is sufficient to maintain body functions such as lung function at an acceptable level. However, this baseline level of drug to blood ratio (or serum blood level) must be raised in order to improve the body function such as lung function during periods of stress such as respiratory difficulty such as an asthma attack and such can be accomplished by the intrapulmonary administration of a drug such as a respiratory drug using the present invention.

Based on the above, it will be understood by those skilled in the art that a plurality of different treatments and means of administration can be used to treat a single patient. For example, a patient can be simultaneously treated with respiratory drug by transdermal administration, respiratory drug via intrapulmonary administration in accordance with the present invention, and drugs which are orally administered.

The device 6 as shown in FIG. 2 and schematically shown within FIG. 9 can be specifically operated as follows. A cassette 5 as shown in FIG. 2 is loaded into the device 6. The device is then armed meaning that the piston such as the spring-loaded piston 24 shown in FIG. 9 is cocked. Further, if applicable, a piston used to force air from the air vents is cocked and, if necessary, a piston used to compress the liquid formulation in the dual container system is cocked. Further, a container of the package is moved into position and the cover 4 is stripped off of the porous membrane. Thereafter, the patient withdraws air from the mouthpiece 9 shown in FIG. 2 and the patient's inhalation profile is developed using the microprocessor. After the inhalation profile is determined, the microprocessor calculates a point within the inhalation profile at which the drug should be released in order to maximize repeatability of the dosing, e.g. by plotting a curve of breath velocity versus time and determining the point on the curve most likely to provide repeatability of dosing. Thereafter, the vibrator is actuated and air is forced through the air vents. While vibration is occurring and air is being released, the device is fired and the formulation contained within the containers is forced through the porous membrane creating an aerosol which is carried into the patient's lungs. The air velocity measuring components continue to read the velocity of the air being withdrawn from the device by the patient while the drug is being delivered. Accordingly, the adequacy of this patient's particular drug delivery maneuver can be determined. All of the events are recorded by the microprocessor. The recorded information can be provided to the caregiver for analysis. For example, the caregiver can determine if the patient correctly carried out the inhalation maneuver in order to correctly delivery drug and can determine if the patient's inhalation profile is effected by the drug (e.g. with respiratory drugs) in order to determine the effectiveness of the drug in treating the patient's particular condition. If necessary, various adjustments can be made such as in the type of drug or the particle size to obtain a particular desired result.

The instant invention is shown herein in what is considered to be the most practical and preferred embodiments. It is recognized, however, that departures may be made therefrom which are within the scope of the invention and that obvious modifications will occur to one skilled in the art upon reading this disclosure.

What is claimed is:

1. A disposable package for use in aerosolized delivery of drugs to the lungs, comprising:

a container having at least one wall which is collapsible by the application of a force and having at least one opening, the container having therein a liquid, flowable formulation which includes a pharmaceutically active drug;

a porous membrane covering the opening wherein the membrane pores have a diameter in the range of from about 0.25 micron to about 6 microns;

wherein the formulation has a viscosity sufficiently low such that the formulation is aerosolized to particles having a diameter of about 0.5 to 12 microns when force is applied to the collapsible wall and moved out of the pores.

2. The disposable package as claimed in claim 1, further comprising a plurality of additional containers wherein each container has at least one wall which is collapsible by the application of a force of 200 psi or less and having at least one opening, and wherein each opening of each additional container is covered with a porous membrane having pores with a diameter in the range of about 0.25 micron to about 6 microns, wherein the additional containers are connected to each other by an interconnecting component.

3. The disposable package as claimed in claim 2, wherein the interconnecting component is in the form of an elongated tape and the pores are present in a pore density of about $1\times10^4$ to about $3\times10^8$ pores/$cm^2$.

4. The disposable package as claimed in claim 1, further comprising barrier separating the formulation from the porous membrane the barrier being rupturable upon the application of a force.

5. The disposable package as claimed in claim 1, wherein a dry pharmaceutically active drug is present in the container, the package further comprising:

an additional container having a flowable liquid therein, the additional container being in fluid connection with the container having the dry drug therein.

6. The disposable package as claimed in claim 5, wherein the additional container is separated from the container having the dry drug therein by a membrane which is ruptured upon the application of pressure in the amount of 10 psi or less.

7. The disposable package of claim 1 wherein the pores of the porous membrane have a conical configuration and are present in a pore density of about $1\times10^4$ to about $3\times10^8$ pores/$cm^2$.

8. The disposable package of claim 1, further comprising a removable cover sheet positioned over the porous membrane, the cover sheet being held in place by a seal.

9. The disposable package of claim 8, further comprising:

an opening in the interconnecting component, positioned next to the porous membrane through which gas may be forced and wherein the seal holding the cover sheet in place is a resealable, releasable adhesive.

10. The disposable package of claim 9, wherein the porous membranes and gas outflow openings are in the shape of elongated rectangles and positioned within a distance of 0.5 cm or less of each other.

11. The disposable package as claimed in claim 1, wherein the porous membrane has a thickness in the range of about 2 to about 20 microns.

12. A disposable package, comprising:

a container having an opening leading to a channel, the container having a liquid, flowable formulation therein which formulation comprises a pharmaceutically active drug, wherein at least one wall of the container is collapsible in a manner so as to allow the formulation in the container to be forced out of the opening into the channel;

a resonance cavity in fluid connection with the container by means of the channel, the resonance cavity having a surface comprising a porous membrane wherein pores of the membrane have a diameter in the range of 0.25 to 6 microns; and an interconnecting component connecting the container and resonance cavity.

13. The disposable package of claim 12, wherein the pores have a cylindrical configuration with each end of the cylinder having a diameter of about 0.25 to 6 microns.

14. The disposable package of claim 12, wherein the pores have a non-cylindrical configuration.

15. The disposable package of claim 14, wherein the pores have a conical configuration with the narrowest point of the configuration having a diameter in the range of about 0.25 to 6 microns.

16. The disposable package of claim 12, wherein the container is collapsible by the application of force to a bottom wall so as to collapse each side wall and can be collapsed by the application of about 20 to about 200 psi in a manner so as to force essentially all of the formulation out of the opening without rupturing the container.

17. The disposable package of claim 12, wherein the interconnecting component connects a plurality of substantially identical containers and resonance cavities.

18. The disposable package unit of claim 12, wherein the pharmaceutically active drug is a respiratory drug.

19. The disposable package of claim 12, wherein the pharmaceutically active drug is asteroid selected from the group consisting of beclamethasone dipropionate, flunisolide, fluticasone, budesonide and triamcinolone acetonide.

20. The disposable package of claim 12, wherein the pharmaceutically active drug is a non-steroidal, anti-inflammatory drug.

21. The disposable package of claim 12, wherein the pharmaceutically active drug is selected from the group consisting of isoproterenol, cromolyn sodium, albuterol sulfate, metaproterenol sulfate salmeterol and formotorol.

* * * * *